United States Patent
Yamamoto et al.

(10) Patent No.: US 10,105,078 B2
(45) Date of Patent: Oct. 23, 2018

(54) METHOD FOR MANAGING HEALTH CONDITION, HEALTH CONDITION MANAGEMENT APPARATUS, AND HEALTH CONDITION MANAGEMENT SYSTEM

(71) Applicant: FUJITSU LIMITED, Kawasaki-shi, Kanagawa (JP)

(72) Inventors: Kiyoko Yamamoto, Kobe (JP); Koji Tatsumi, Daito (JP); Yosuke Senta, Kawasaki (JP); Shigeo Takenaka, Sakai (JP); Atsuko Kawai, Izumi (JP)

(73) Assignee: FUJITSU LIMITED, Kawasaki (JP)

( * ) Notice: Subject to any disclaimer, the term of this patent is extended or adjusted under 35 U.S.C. 154(b) by 444 days.

(21) Appl. No.: 14/877,185

(22) Filed: Oct. 7, 2015

(65) Prior Publication Data
US 2016/0135716 A1    May 19, 2016

(30) Foreign Application Priority Data
Nov. 19, 2014   (JP) ................. 2014-235082

(51) Int. Cl.
*A61B 5/103*   (2006.01)
*A61B 5/00*    (2006.01)
*A61B 5/11*    (2006.01)

(52) U.S. Cl.
CPC ............ *A61B 5/112* (2013.01); *A61B 5/6823* (2013.01); *A61B 2503/40* (2013.01); *A61B 2562/0219* (2013.01)

(58) Field of Classification Search
CPC .... A61B 5/112; A61B 5/6823; A61B 2503/40
See application file for complete search history.

(56) References Cited

U.S. PATENT DOCUMENTS

| | | | |
|---|---|---|---|
| 2008/0021352 A1* | 1/2008 | Keegan | A61B 5/0002 600/595 |
| 2012/0274442 A1* | 11/2012 | Mottram | A01K 29/005 340/5.8 |
| 2013/0217980 A1* | 8/2013 | Elser | A61B 5/08 600/301 |

FOREIGN PATENT DOCUMENTS

JP    2010-282456    12/2010

OTHER PUBLICATIONS

Buchner, H.H.F. (1995). Temporal stride patterns in horses with experimentally induced fore—or hindlimb lameness. Equine veterinary journal, 27(S18), 161-165.*
Equinosis (2011). Lameness Locator: User Manual. pp. 1-63. Retrieved from equinosis.com.*

* cited by examiner

*Primary Examiner* — Jeffrey G Hoekstra
*Assistant Examiner* — Nicholas E Kolderman
(74) *Attorney, Agent, or Firm* — Staas & Halsey LLP

(57) ABSTRACT

A method for causing a computer to execute a process for managing health condition, the process includes: detecting a grounding timing of a leg of a quadruped and a timing of weight-shift to a rear side of the quadruped; and determining whether or not the leg of the quadruped has a disease or injury, based on the detected grounding timing of the leg of the quadruped and the detected timing of a weight-shift to the rear side of the quadruped.

15 Claims, 20 Drawing Sheets

FIG. 3

| MEDICAL CHART NO. | NAME OF HORSE | SENSOR SETS ID | NOTIFICATION DESTINATION ADDRESS | DETERMINATION DATE AND DETERMINATION RESULT OF HEALTH CONDITION OF LEG | REMARKS |
|---|---|---|---|---|---|
| 0001 | ○○○○○○○○ | SS01 | ADDRESS α | Y1/M1/D1 PROBLEM ABSENCE | |
| 0002 | ×××××× | SS02 | ADDRESS α | Y1/M1/D1 PROBLEM EXISTS IN RIGHT FRONT LEG | Y1/M1/D2 PROCESS TERMINATED |
| 0003 | ◆◆◆◆◆◆ | SS03 | ADDRESS β | Y1/M1/D1 PROBLEM EXISTS IN HIND LEG | Y1/M1/D3 UNDER TREATMENT |
| ... | ... | ... | ... | ... | ... |

| | OBJECT OF OBTAINING DATA | DATA TO BE OBTAINED | ATTACHMENT POSITION |
|---|---|---|---|
| FIRST SENSOR | DETECTING GROUNDING TIMING OF RIGHT FRONT LEG | COMPONENT IN VERTICAL DIRECTION OF ACCELERATION OF RIGHT FRONT LEG | RIGHT SIDE OF ABDOMEN OR RIGHT SIDE OF CHEST |
| SECOND SENSOR | DETECTING GROUNDING TIMING OF LEFT FRONT LEG | COMPONENT IN VERTICAL DIRECTION OF ACCELERATION OF LEFT FRONT LEG | LEFT SIDE OF ABDOMEN OR LEFT SIDE OF CHEST |
| THIRD SENSOR | DETECTING TIMING OF WEIGHT SHIFT TO REAR SIDE | COMPONENT IN VERTICAL DIRECTION OF ACCELERATION OF HEAD | NECK, CHEST, OR HEAD |

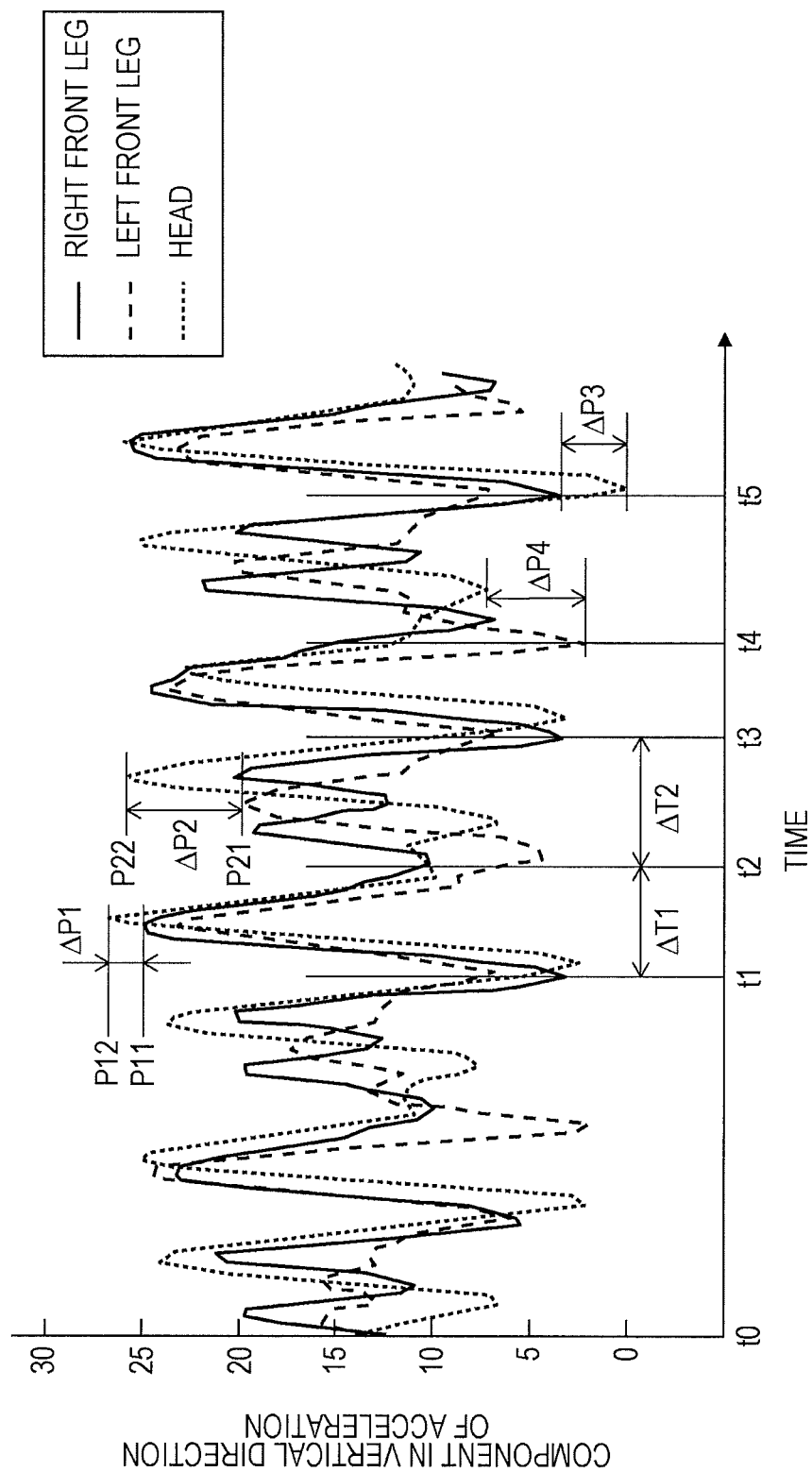

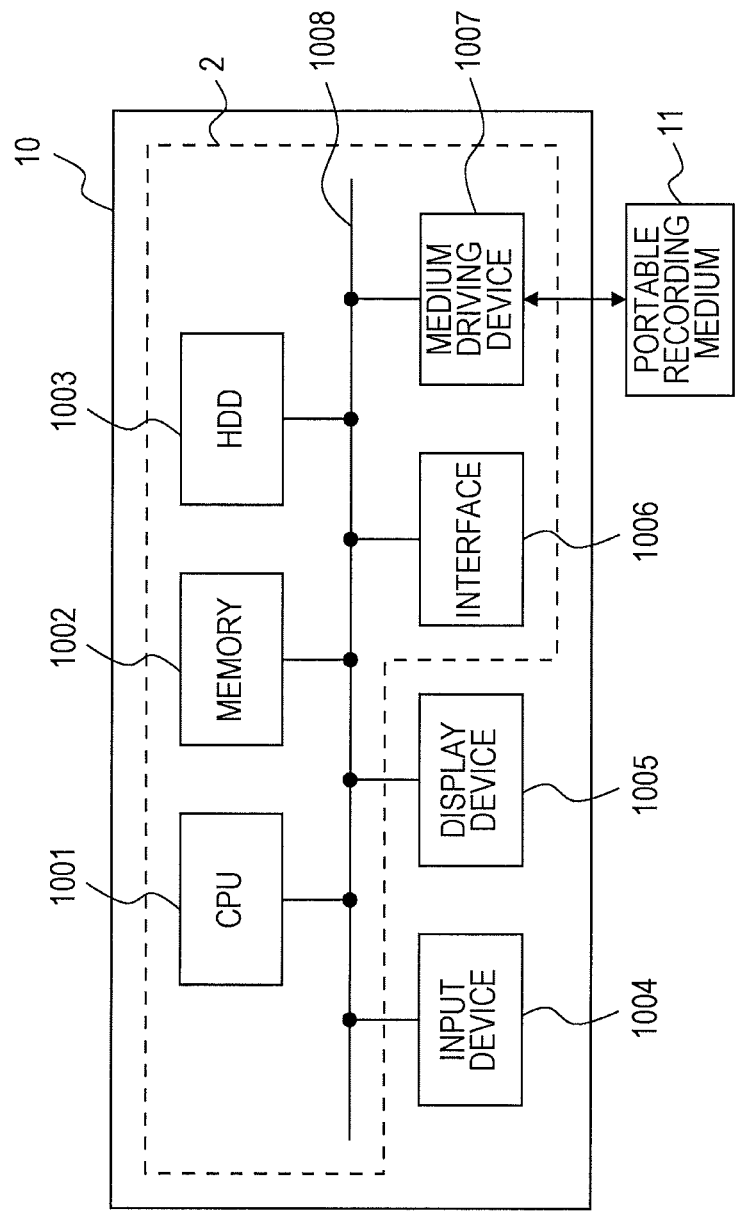

FIG. 11

| | OBJECT OF OBTAINING DATA | DATA TO BE OBTAINED | ATTACHMENT POSITION |
|---|---|---|---|
| FIRST SENSOR | DETECTING AND SPECIFYING GROUNDING TIMING OF RIGHT FRONT LEG AND LEFT FRONT LEG | COMPONENT IN VERTICAL DIRECTION OF ACCELERATION OF ONE FRONT LEG | RIGHT SIDE OF ABDOMEN OR LEFT SIDE OF CHEST |
| SECOND SENSOR | DETECTING TIMING OF WEIGHT SHIFT TO REAR SIDE | COMPONENT IN VERTICAL DIRECTION OF ACCELERATION OF HEAD | NECK, CHEST, OR HEAD |

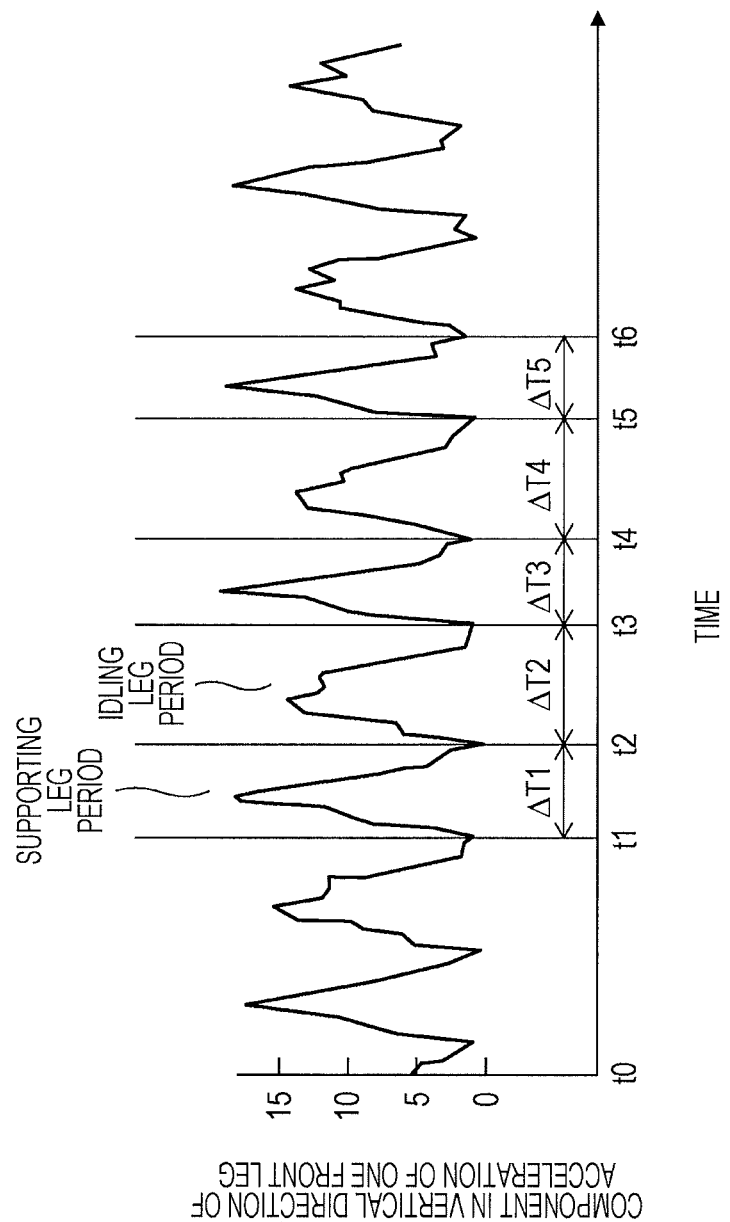

FIG. 17

|  | OBJECT OF OBTAINING DATA | DATA TO BE OBTAINED | ATTACHMENT POSITION |
|---|---|---|---|
| FIRST SENSOR | DETECTING GROUNDING TIMINGS OF BOTH FRONT LEGS | COMPONENT IN VERTICAL DIRECTION OF ACCELERATION OF CHEST POSITION | CENTER OF CHEST |
| SECOND SENSOR | SPECIFYING GROUNDING TIMINGS OF RIGHT AND LEFT FRONT LEGS | COMPONENT IN VERTICAL DIRECTION OF ANGULAR VELOCITY OF CHEST POSITION | CENTER OF CHEST |
| THIRD SENSOR | DETECTING TIMINGS OF WEIGHT SHIFT TO REAR SIDE | COMPONENT IN VERTICAL DIRECTION OF ACCELERATION OF HEAD | NECK, CHEST, OR HEAD |

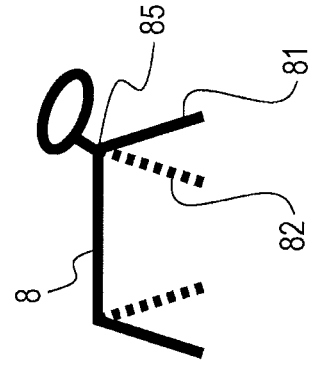
FIG. 19A1
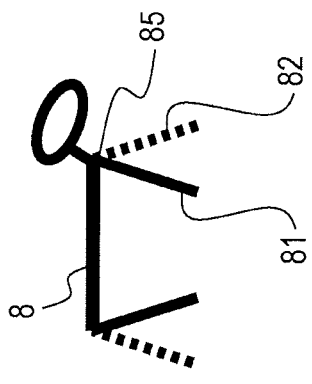
FIG. 19B1
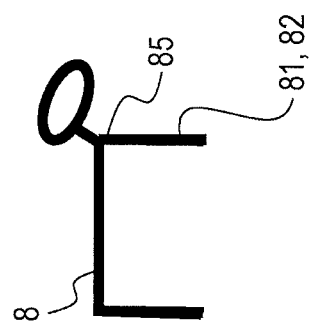
FIG. 19C1
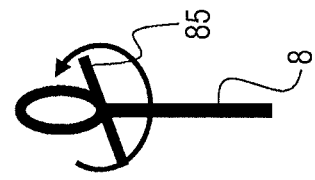
FIG. 19A2
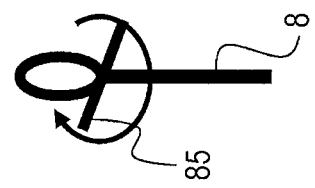
FIG. 19B2
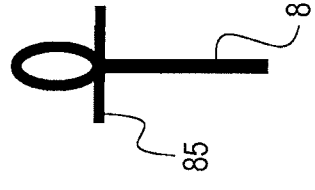
FIG. 19C2

METHOD FOR MANAGING HEALTH CONDITION, HEALTH CONDITION MANAGEMENT APPARATUS, AND HEALTH CONDITION MANAGEMENT SYSTEM

CROSS-REFERENCE TO RELATED APPLICATION

This application is based upon and claims the benefit of priority of the prior Japanese Patent Application No. 2014-235082, filed on Nov. 19, 2014, the entire contents of which are incorporated herein by reference.

FIELD

The embodiments discussed herein are related to a health condition management apparatus, a health condition management system, and a health condition management method for a quadruped.

BACKGROUND

As a quadruped, there is an animal such as a racehorse or a riding horse bred (raised) in an environment in which a management system such as a health management is prepared. Hereinafter, the racehorse is exemplified.

One of the health management of a racehorse is checking a health condition of its legs. When a problem of inflammation, or the like occurs in its leg, it takes time to treat when a symptom progresses (worsens). In addition, when the problem occurs in its leg, the horse walks and runs while protecting the leg, and therefore, there is a concern that the problem also occurs in its other legs. For this reason, since the management of the health condition of a leg of the horse is considered important when breeding a racehorse, early detection of a problem of disease, injury, or the like is desirable.

The health condition of the leg of the racehorse is managed, for example, by having a veterinarian perform regular medical examinations on the leg of the horse. However, when the leg has an early mild inflammation, and the like, it is not easy to find the problem by only visual inspection or a palpation. For this reason, as an object such as supporting early detection of the problem of the leg, a method has been studied in which whether or not the leg has the problem is determined based on a balance between a right and left sides in respect to the body of horse.

In addition, as one of management methods of the health condition of the racehorse, there is a method in which the health condition is determined and managed based on output data of a sensor attached to the horse (for example, referring to Japanese Laid-open Patent Publication No. 2010-282456). In such a management method, the sensor such as an acceleration sensor, or the like is mounted to the leg or the neck of the horse, and the health condition is determined by comparing current operation data calculated based on measured data of the sensor with operation data of a normal state obtained in advance.

SUMMARY

According to an aspect of the invention, a method for causing a computer to execute a process for managing health condition, the process includes detecting a grounding timing of a leg of a quadruped and a timing of weight-shift to a rear side of the quadruped; and determining whether or not the leg of the quadruped has a disease or injury, based on the detected grounding timing of the leg of the quadruped and the detected timing of a weight-shift to the rear side of the quadruped.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 3 is a schematic diagram illustrating an example of a medical chart DB;

FIG. 4 is a diagram describing an object of obtaining data of a first sensor to a third sensor in the first embodiment;

FIG. 9 is a graph describing a specific example of a determination method of the leg having the problem in the health condition in the first embodiment;

FIG. 10 is a schematic diagram illustrating a hardware configuration of a health condition management apparatus;

FIG. 11 is a diagram describing an object of obtaining data of the first sensor and the second sensor in a determination method of a health condition of legs of a horse according to a second embodiment;

FIG. 15 is a graph describing a method of specifying the grounding timing of a right front leg and a left front leg;

FIG. 17 is a diagram describing an object of obtaining data of the first sensor to the third sensor in a determination method of a health condition of legs of a horse according to a third embodiment;

FIGS. 19A1 to 19C2 are schematic diagrams describing a relationship between the gait and a rotation in a yaw-axis direction of the chest of a horse.

DESCRIPTION OF EMBODIMENTS

In a method investigating the balance between the right and the left sides described in the background, it is recognized that a problem of inflammation, or the like occurs in the leg by deterioration of the balance between the right and the left sides, but it is not recognized which leg has the problem. Therefore, when deterioration of the balance between the right and left sides is determined, medical examinations have to be performed on all four legs. Particularly, when a cause is not possible to be easily specified by a visual inspection or a palpation, a detailed examination is performed using medical diagnostic equipment. For this reason, since effort is spent and time is taken for specifying the leg having the problem, the racehorse feels undesirable stress.

Further, in the method of specifying the health condition based on the measured data of the sensor mounted on the horse, the operation data in a normal state have to be obtained in advance.

However, in order to obtain the operation data in the normal state, it is desirable to recognize that the horse is in a normal state. In addition, even in a normal state, the way in which the horse moves its leg is different depending on horse gait or on which one of the right front leg and the left front leg is leading. Accordingly, it takes effort and time to obtain the operation data in the normal state.

Accordingly, it is desired to support a detection of a disease or injury in a leg of a four-footed animal (quadruped).

Hereinafter, embodiments will be described with reference to drawings.

First Embodiment

Figure 1:
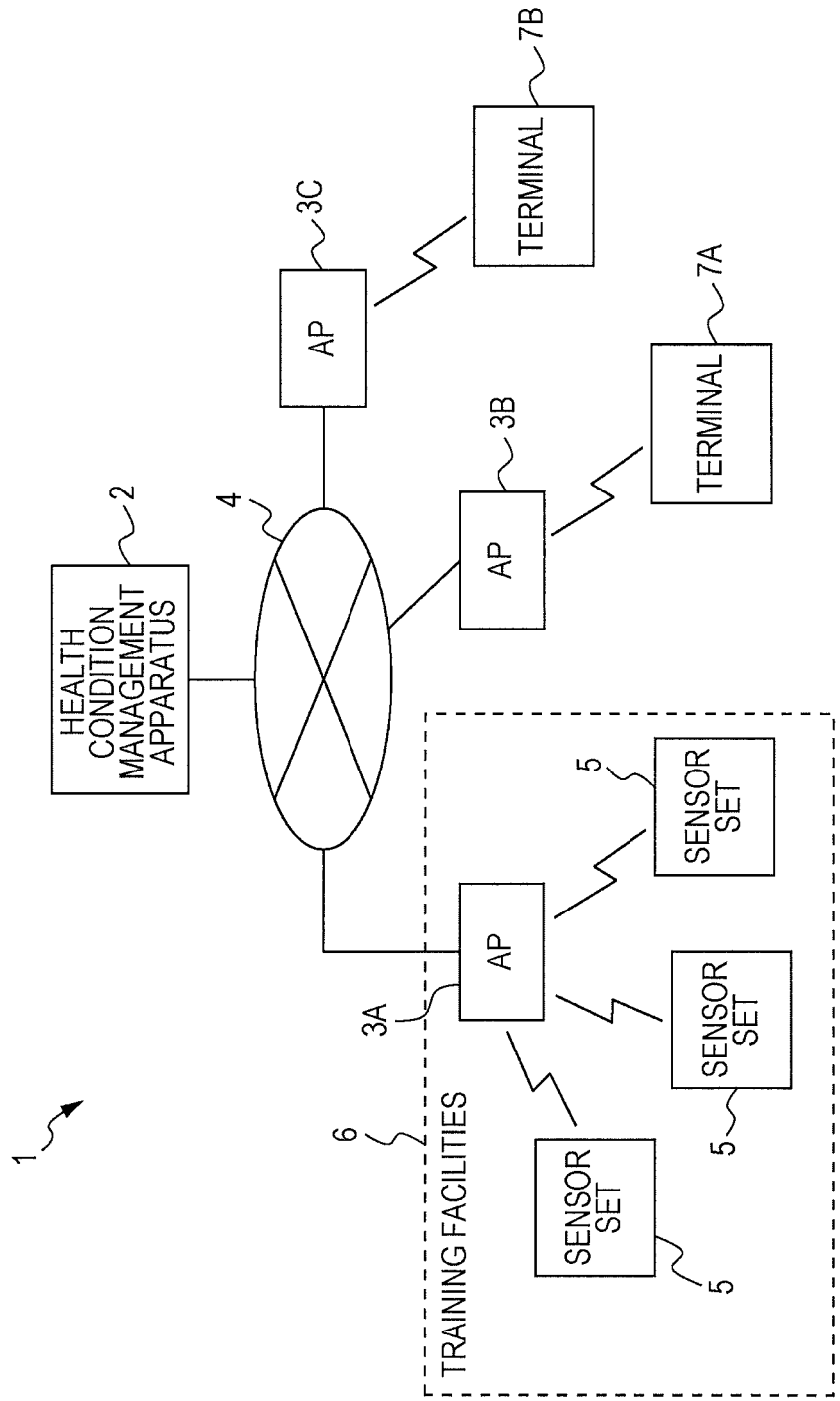
FIG. 1 is a schematic diagram illustrating a configuration example of a health condition management system according to a first embodiment.

FIG. 1 is a schematic diagram illustrating a configuration example of a health condition management system according to a first embodiment.

The health condition management system according to the first embodiment, for example, is a system that manages a health condition of a racehorse, and includes a function for determining the health condition of the leg of the racehorse.

As illustrated in FIG. 1, the health condition management system 1 includes a health condition management apparatus 2, a first access point 3A, and a first to a third sensor sets 5.

The health condition management apparatus 2 and the first access point 3A are communicably coupled to each other through a network 4 such as the Internet.

Radio communication is performed between the first access point 3A and each of the first to the third sensor sets 5, and the first access point 3A relays a transmission of a measured result from each of the sensor sets 5 to the health condition management apparatus 2. The first access point 3A is installed in, for example, training facilities 6 for training the racehorse. In addition, the first access point 3A is realized as a mobile terminal such as a smart phone, which may be carried by a rider or a trainer.

In addition, the health condition management apparatus 2 is communicably coupled to a second access point 3B and a third access point 3C through the network 4. The second access point 3B and the third access point 3C are, for example, access points of a wireless LAN or a base station of a mobile phone. The second access point 3B and the third access point 3C relay a connection of the network 4 and terminals 7A and 7B which are able to perform the radio communication according to a radio communication standard of each access point. As the terminals 7A and 7B, for example, there are the mobile phone, the smart phone, a personal computer, and the like. Moreover, the terminals 7A and 7B, which are coupled to the network 4 through the second access point 3B and the third access point 3C, are able to be coupled to the health condition management apparatus 2 only in a case in which connection to the health condition management apparatus 2 is allowed.

Figure 2:
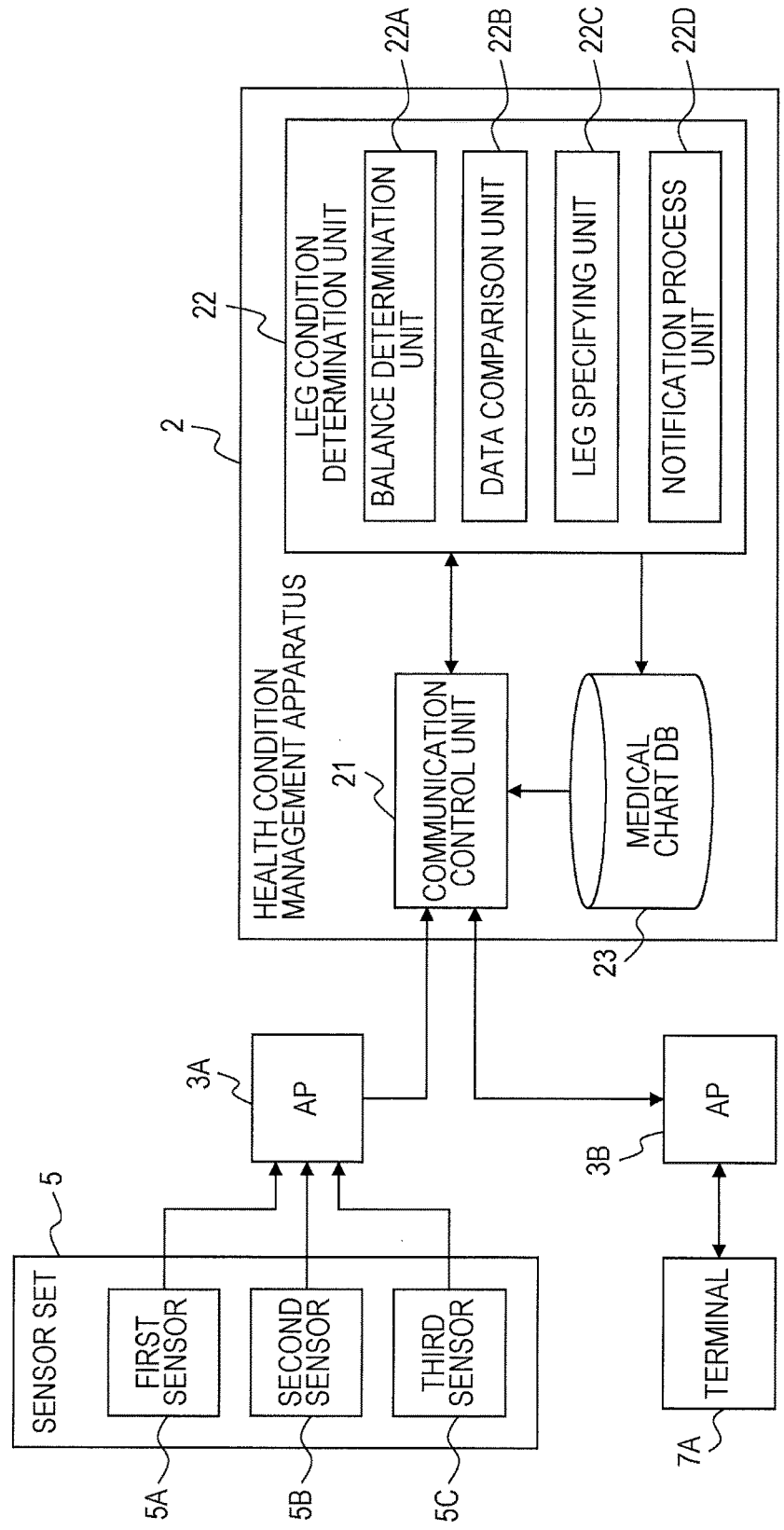
FIG. 2 is a functional block diagram illustrating a configuration of a health condition management apparatus and a sensor set.

FIG. 2 is a functional block diagram illustrating a configuration of the health condition management apparatus and the sensor set. The health condition management apparatus 2 includes, a communication control unit 21, a leg condition determination unit 22, and a medical chart (or a medical record) DB 23, as illustrated in FIG. 2.

The communication control unit 21 controls communication of the first access point 3A, and the like through the network 4. The communication control unit 21 establishes a connection with the first access point 3A, for example, according to a preset schedule, and obtains measured results of each of the sensor sets 5. In addition, the communication control unit 21 transmits a notification (for example, e-mail) including information relating to the health condition of the leg of the horse to a predetermined address. Further, the communication control unit 21 communicates with the terminal 7A when receiving a connection request from the terminal 7A which has been allowed to access to the health condition management apparatus 2 in advance, and provides, for example, medical chart information registered at the medical chart DB 23 to the terminal 7A.

The leg condition determination unit 22 determines the health condition of the leg of the horse based on the obtained measured result of each of the sensor sets 5. The leg condition determination unit 22 includes a balance determination unit 22A, a data comparison unit 22B, a leg specifying unit 22C, and a notification process unit 22D. The balance determination unit 22A determines whether or not a problem occurs in a balance between the right and the left sides of the horse. The data comparison unit 22B investigates that a vertical movement of the horse's neck associated with the problem of the leg (disease, injury, or the like) periodically occurs, by comparing the measured results of a first sensor 5A to a third sensor 5C with each other. The leg specifying unit 22C specifies which of a right front leg, a left front leg, or either of the hind legs has the problem when the vertical movement of the neck associated with the problem of the leg periodically occurs. The notification process unit 22D generates a message for notifying which leg has the problem when the problem occurs in the leg, and transmits the message to a predetermined address through the communication control unit 21.

The medical chart DB 23 is a database in which there is recorded the medical chart or the medical record of each horse including a determination result, such as the health condition of the leg, of the leg condition determination unit 22.

FIG. 3 is a schematic diagram illustrating an example of the medical chart DB. As illustrated in FIG. 3, the medical chart DB 23 includes a medical chart number, a name of horse, a sensor set ID, a notification destination address, and a determination date and a determination result of the health condition of the leg, and remarks.

The medical chart number is an identification number that identifies one of a plurality of the medical charts for managing the health condition in one health condition management apparatus 2. The name of the horse is a name of the horse whose the health condition is managed in each medical chart. The sensor set ID is an identification number that identifies the sensor set used for determining each health condition of the leg of the horse. The notification destination address is an address, such as transmission destination address, of the message for notifying a case in which the problem occurs in the health condition of the leg, and for example, an e-mail address. The determination date and the determination result of the health condition of the leg are a new or a recent determination date and determination result in regard to the health condition of the leg. The remarks are a recording of process after notifying the occurrence of the problem in the leg.

When a new determination result has a problem in the right front leg as described in the medical chart of 0002 illustrated in FIG. 3, for example, in the message having an address α as an address at a new determination date (Y1 year M1 month D1 day), it notifies that the right front leg of a horse having a name of "xxxxxx" has the problem. A person, for example, veterinarian, trainer, or the like who receives and reads the message with the terminal performs a predetermined process after receiving the message and then writes contents of the process or a present situation into the remarks of the medical chart using the terminal.

Moreover, only the determination result in regard to the health condition of the leg is recorded in the medical chart DB 23 illustrated in FIG. 3; however, the medical chart DB 23 is not limited thereto, and a health condition of a region other than the leg may also be recorded together in the medical chart DB 23.

Next, the sensor sets 5 illustrated in FIG. 2 will be described. Each of the sensor sets 5 measures data which is desirable to determine the health condition of the leg of the horse, and in the embodiment, one sensor set 5 includes a first sensor 5A to a third sensor 5C. A function and an attaching position of the first sensor 5A to the third sensor 5C in the embodiment will be described with reference to FIG. 4 and FIG. 5.

Figure 5:
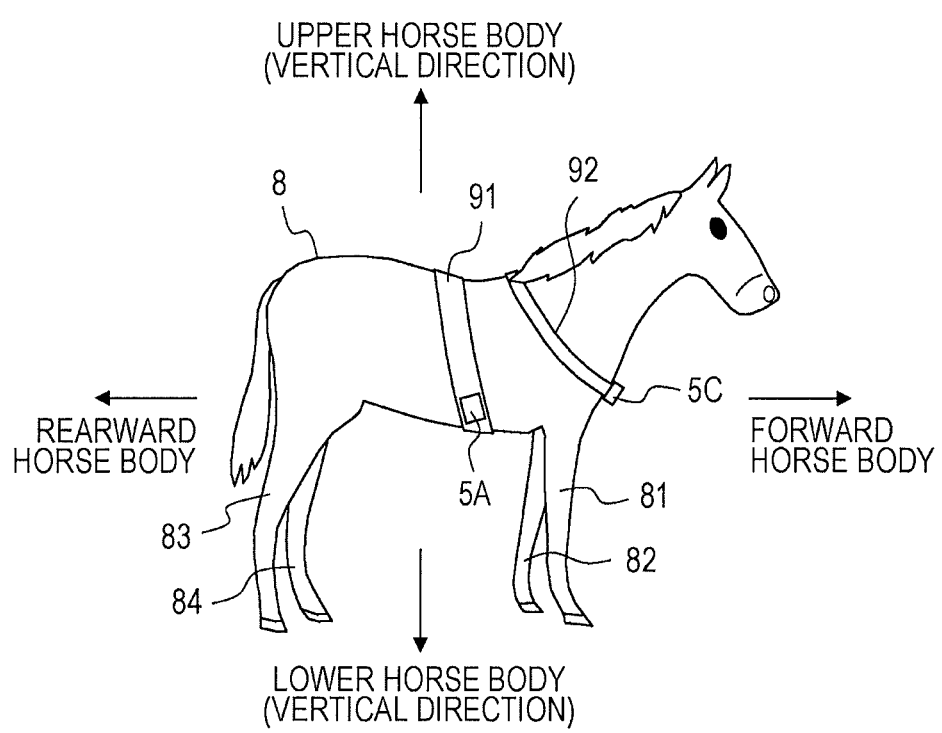
FIG. 5 is a schematic diagram illustrating the definitions of the right, left, top and bottom of a horse's body, and an attaching method of the first sensor to the third sensor to the horse's body.

FIG. 4 is a diagram describing an object of obtaining data of the first sensor to the third sensor in the first embodiment. FIG. 5 is a schematic diagram illustrating a definition of right, left, top and bottom of a horse body, and an attaching method of the first sensor to the third sensor to the horse body.

The first sensor 5A and the second sensor 5B respectively obtains data for detecting a grounding timing of the right front leg and a grounding timing of the left front leg as illustrated in FIG. 4. A grounding timing of a leg is a timing at which the leg contacts a ground or lands on the ground. As a method of detecting the grounding timing of the leg, there are various methods; however, in the embodiment, the ground timing is detected from a time change of the vertical movement of the leg (moving of horse body in vertical direction). For this object, the first sensor 5A and the second sensor 5B respectively obtains a vertical direction component of acceleration of the right front leg and a vertical direction component of acceleration of the left front leg. Accordingly, an acceleration sensor is used as each of the first sensor 5A and the second sensor 5B.

As illustrated in FIG. 4, the third sensor obtains data for detecting the timing of weight-shift to a rear side of the horse body. As a detecting method of the timing of the weight-shift, there are various methods; however, in the embodiment, the timing of the weight-shift is detected from the time change of the vertical movement of the neck (moving of horse body in vertical direction). For this object, the third sensor obtains the vertical direction component of the acceleration of the neck. Accordingly, the acceleration sensor is used as the third sensor. In a following description, the vertical direction component of the acceleration is referred to as a "vertical acceleration".

Moreover, in the embodiment, as illustrated in FIG. 5, a vertically upward direction and a vertically downward direction in a state in which a horse 8 standing on its four legs 81 to 84 are respectively referred to as an upper side of the horse body and a lower side of the horse body. In addition, a direction of the hind legs 83 and 84 viewed from the front legs 81 and 82 is referred to as a rear side of the horse body, and a direction opposite to the direction of the hind legs 83 and 84 viewed from the front legs 81 and 82 is referred to as the front side of the horse body. Further, a right side and a left side of which the horse body standing on the four legs 81 to 84 faces the front side are respectively referred to as a right horse body and a left horse body.

In order to measure the acceleration of the right front leg, the first sensor 5A is mounted on a region, in the horse 8, with which the vertical movement of the right front leg 81 is associated, for example, a right side of an abdomen or the right side of the chest of the horse 8. In addition, in order to measure the acceleration of the left front leg, the second sensor 5B is mounted on a region, in the horse 8, with which the vertical movement of the left front leg 82 is associated, for example, a left side of the abdomen or a left side of the chest. At that time, the first sensor 5A and the second sensor 5B are mounted on any one of the abdomen and the chest. That is, when the first sensor 5A is mounted on the right side of the abdomen, the second sensor 5B is mounted on the left side of the abdomen.

When the first sensor 5A and the second sensor 5B are mounted on the abdomen, the first sensor 5A and the second sensor 5B are attached to a surcingle 91 (referring to FIG. 5). The surcingle 91 is a belt (auxiliary tool) which is used at the time of fixing a position of a saddle loaded on the back of the horse 8. For this reason, when the first sensor 5A and the second sensor 5B are attached to the surcingle 91, for example, compared to a case in which both sensors are mounted on the front leg, discomfort to the horse due to mounting of the sensor may be reduced. In addition, safety is improved in comparison with a case in which the sensor is mounted on the front leg.

There are various methods for attaching the first sensor 5A and the second sensor 5B to the surcingle 91. For example, a method of inserting and attaching each sensor into pockets installed in the surcingle 91 which are positioned on the right and left sides of the abdomen of the horse 8. In addition, for example, the first sensor 5A and the second sensor 5B may be attached to the surcingle 91 using a hook and loop fastener.

The third sensor 5C that measures the acceleration of the neck is mounted on a region, in the horse 8, with which the vertical movement of the neck is associated. The region is, for example, the neck, the chest, or a head of the horse 8. In the embodiment, as illustrated in FIG. 5, the third sensor 5C is mounted on the chest using a breast collar 92. The breast collar 92 is an auxiliary tool that is the same as the surcingle 91, and which is used at the time of fixing the position of a saddle. For this reason, when the third sensor 5C is attached to the breast collar 92, and the discomfort to the horse due to mounting of the sensor may be reduced.

When the third sensor 5C is attached to the breast collar 92, for example, the third sensor 5C is inserted and attached to a pocket installed in the breast collar 92. In addition, the third sensor 5C may be attached to the breast collar 92, for example, using a hook and loop fastener.

As described above, as each of the first sensor 5A to the third sensor 5C, the acceleration sensor is used. In addition, the first sensor 5A to the third sensor 5C respectively wirelessly-communicate with the first access point 3A (referring to FIG. 1 and FIG. 2), and the first access point 3A transmit the measurement value (acceleration data) to the health condition management apparatus 2. For this reason, as the first sensor 5A to the third sensor 5C, for example, an acceleration sensor in which a radio communication control unit (not illustrated) for wirelessly-communicating with the first access point 3A is mounted is used. In addition, in place of the acceleration sensor in which a radio communication control unit is mounted, a small radio communication apparatus may be connected (externally) to each of the first sensor 5A to the third sensor 5C.

In addition, each of the sensors 5A to 5C also transmits identification information including sensor set IDs so as to correspond to three measurement values measured by the first sensor 5A to the third sensor 5C of one of the sensor sets 5 in the health condition management apparatus 2.

In addition, the first sensor 5A to the third sensor 5C, for example, may transmit the measurement value to the health condition management apparatus 2 whenever outputting the measurement value, or may transmit the measurement value to the health condition management apparatus 2 by accumulating the measurement value obtained during a certain period (for example, a few minutes to several tens of minutes) in the sensor.

Hereinafter, a determination method of the health condition of the leg of the horse in the health condition management apparatus of the embodiment will be described with reference to FIG. 2, FIG. 6, and FIG. 7.

Figure 6:
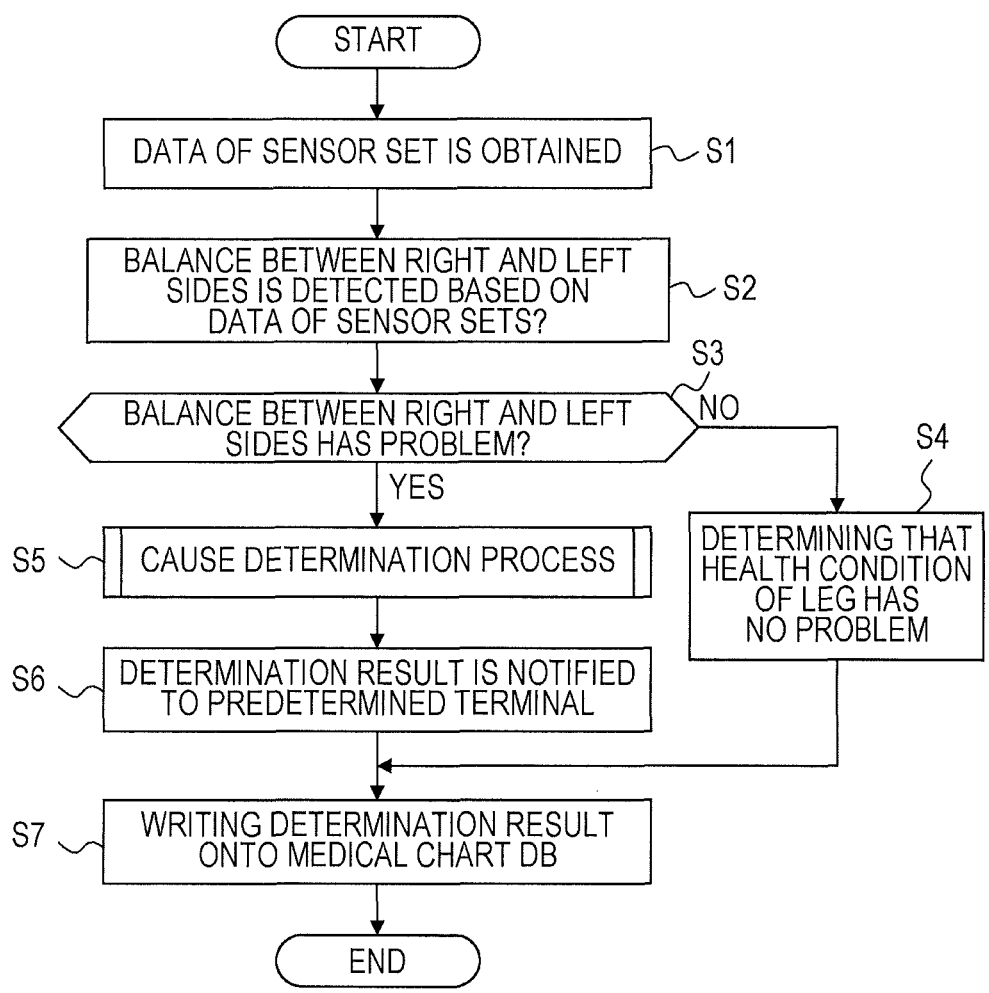
FIG. 6 is a flow chart illustrating a determination method of the health condition of the legs of a horse according to the first embodiment.

FIG. 6 is a flow chart illustrating the determination method of the health condition of the leg of the horse according to the first embodiment. FIG. 7 is a flow chart illustrating contents of a cause determination process of FIG. 6.

In the determination method of the health condition of the leg of the embodiment, as illustrated in FIG. 6, first, the data from the sensor sets 5 is obtained (Step S1). A process of Step S1 is performed by the communication control unit 21 of the health condition management apparatus 2. The communication control unit 21 obtains the acceleration data received from the first sensor 5A to the third sensor 5C of the sensor sets 5 by corresponding to the sensor set ID.

When the acceleration data is obtained from the sensor sets 5, the health condition management apparatus 2, next, calculates a balance between the right and the left sides of the horse body based on the obtained data (Step S2), and determines whether or not there is a problem in the balance between the right and the left sides (Step S3). Processes of Steps S2 and S3 are performed by the balance determination unit 22A of the leg condition determination unit 22 illustrated in FIG. 2. The balance determination unit 22A, for example, calculates the balance between the right and left sides of the horse body and determines whether or not the problem occurs, using the vertical acceleration data of the right front leg (vertical direction component of acceleration data) obtained from the first sensor 5A and the vertical acceleration data of the left front leg obtained from the second sensor 5B.

The determination method of balance between the right and left sides may be performed by any one of well-known methods. For example, while data of one step is extracted from the vertical acceleration data of the right leg and data immediately before (one step before) the right leg is extracted from the vertical acceleration data of the left leg, and symmetric property, as degree of similarity, between waveforms corresponding to two sets of the extracted data is calculated. When the symmetric property between the waveforms is lower than a preset threshold, the balance between the right and left sides deteriorates, that is, it is determined that the balance between the right and left sides has the problem. In addition, the balance between the right and left sides, for example, may be determined by comparing an area of a region of a positive value in the data of one step of the vertical acceleration data of the right leg, with an area of a region of the positive value in the data of one step of the vertical acceleration data of the left leg immediately before the right leg (one step before).

When the balance between the right and the left sides does not have a problem (No in Step S3), the balance determination unit 22A determines that the health condition of the leg does not have the problem (Step S4). Then, the balance determination unit 22A records the determination result into the medical chart DB 23 (Step S7), and there is terminated a determination process in regard to the health condition of the leg of the horse corresponding to the sensor set ID obtained in Step S1. In Step S7, a column of the determination date and the determination result of the medical chart No. corresponding to the sensor set ID obtained in Step S1 are updated. In addition, when writing the determination date and the determination result into the medical chart DB 23, for example, the determination result during recent several weeks to several months may be accumulated.

Meanwhile, when the balance between the right and the left sides has the problem (Yes in Step S3), the cause determination process of determining which leg has a cause of the problem is performed (Step S5). The cause determination process of Step S5 is performed by cooperating the data comparison unit 22B and the leg specifying unit 22C of the leg condition determination unit 22. The cause determination process will be described with reference to FIG. 7.

Figure 7:
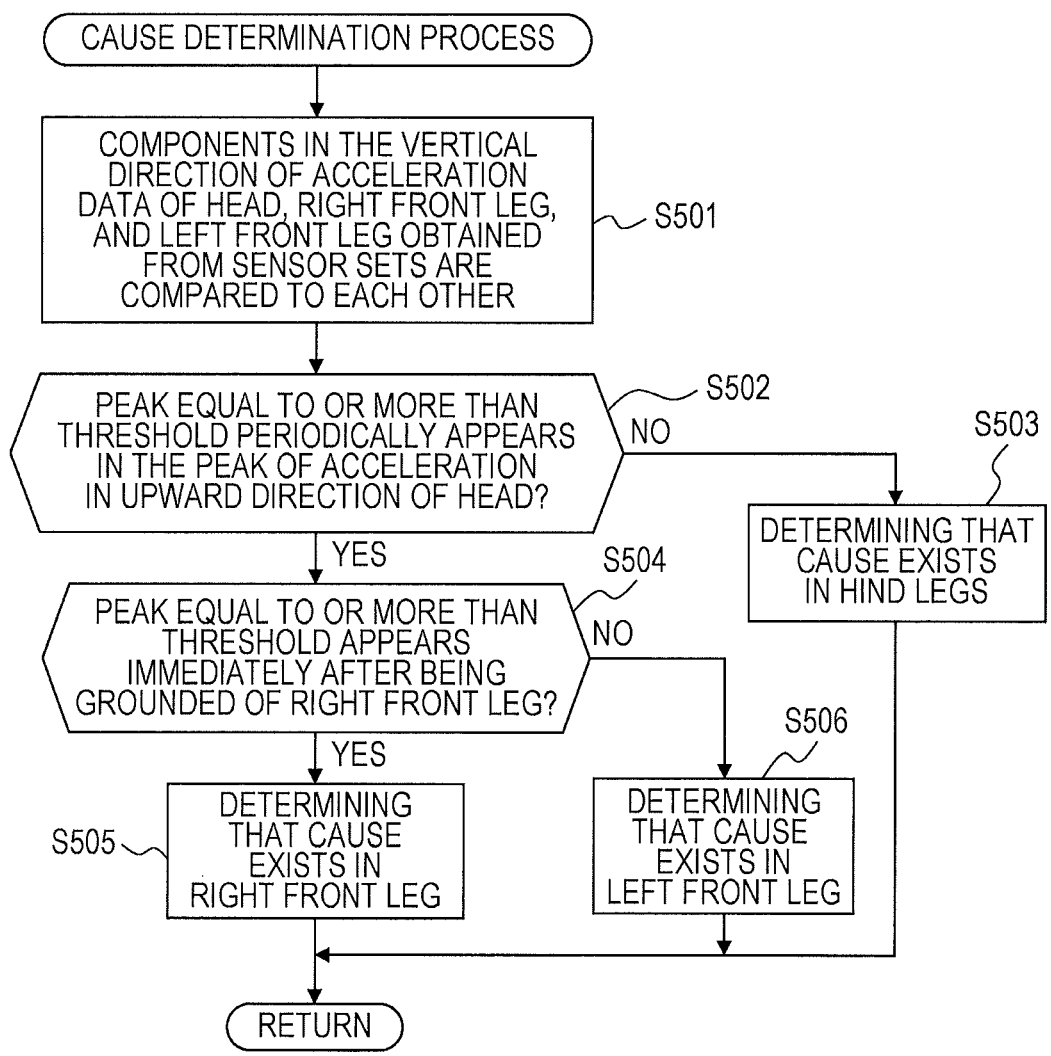
FIG. 7 is a flow chart illustrating contents of a cause determination process of FIG. 6.

In the cause determination process, as illustrated in FIG. 7, first, the vertical direction components of the acceleration data of the neck, the right front leg, and the left front leg obtained from the sensor sets 5 are compared to each other (Step S501). A process of Step S501 is performed by the data comparison unit 22B. The data comparison unit 22B synchronizes three sets of vertical acceleration data, for example, based on a time stamp in each of the vertical acceleration data (vertical direction component of acceleration data). In addition, the data comparison unit 22B compares these three sets of the vertical acceleration data with each other, and then investigates a following (1) and (2).

(1) A difference ΔP1 between a value P11 of a peak (upwardly convex peak) of the acceleration in an upward direction of the right front leg which appears immediately after the timing when the right front leg is grounded and a value P12 of a peak of the acceleration is in an upward direction of the neck.

(2) A difference ΔP2 between a value P21 of a peak of the acceleration in an upward direction of the left front leg which appears immediately after the timing when the left front leg is grounded and a value P22 of a peak of the acceleration is in an upward direction of the neck.

Moreover, the period of "time immediately after the timing when the right front leg is grounded" means a period from being grounded of the right front leg to initially being grounded of the left front leg. In the same manner, a period of "time immediately after the timing when the left front leg is grounded" means a period of time from grounding the left front leg to initially grounding of the right front leg.

In addition, the peak of the acceleration in the upward direction may be calculated using well-known methods. In addition, the above described (1) and (2), for example, are investigated from each of the timings when the front leg is grounded multiple times in the vertical acceleration data during a few seconds to several tens of seconds.

When the above described (1) and (2) are investigated in comparison with three sets of the vertical acceleration data, next, it is determined that a peak equal to or more than the threshold periodically appears in the peak of the acceleration in the upward direction of the neck (Step S502). A process in Step S502 is performed by the leg specifying unit 22C. The leg specifying unit 22C determines whether or not an absolute value of each of the differences ΔP1 and ΔP2 described above is equal to or more than the threshold. The threshold in the process of Step S502 may be suitably set based on a difference with a normal case in which the problem in the leg such as an inflammation, and the like does not exist, is used as a reference.

When the peak equal to or more than the threshold does not periodically appear (No in Step S502), the leg specifying unit 22C determines that a cause of a problem that occurs in the balance between the right and the left sides exists in hind legs (Step S503), and then the cause determination process is terminated in which the process is shifted to "return".

Meanwhile, when the peak equal to or more than the threshold periodically appears (Yes in Step S502), the leg specifying unit 22C, next, determines whether or not the peak equal to or more than the threshold is appears immediately after the right front leg is grounded (Step S504). In the determination in Step S504, when the absolute value of the difference ΔP1 of the value of the peak above described is equal to or more than the threshold, it is determined that the peak equal to or more than the threshold appears immediately after the right front leg is grounded. When the peak equal to or more than the threshold appears immediately after the right front leg is grounded (Yes in Step S504), the leg specifying unit 22C determines that the cause of the problem that occurs in the balance between the right and the left sides exists in the right front leg (Step S505), and then the cause determination process is terminated in which the process is shifted to "return". In addition, when the peak equal to or more than the threshold does not appear immediately after the right front leg is grounded (No in Step S504), the leg specifying unit 22C determines that the cause exists in the left front leg (Step S506), and then the cause determination process is terminated in which the process is shifted to "return".

When determining that the cause of the problem that occurs in the balance between the right and the left sides exists in the leg (that is, leg having problem of inflammation, or the like) in the cause determination process, next, the determination result is notified to a predetermined terminal (Step S6). The process of Step S6 is performed by the notification process unit 22D of the leg condition determination unit 22. The notification process unit 22D generates a notification message including the determination date and the determination result (leg having problem). An address of the notification message, for example, is a notification destination address registered in the medical chart of the medical chart number corresponding to the sensor set ID obtained in Step S1. The generated notification message is transmitted from the communication control unit 21 to a predetermined terminal or a mail server in the network 4.

Figure 8:
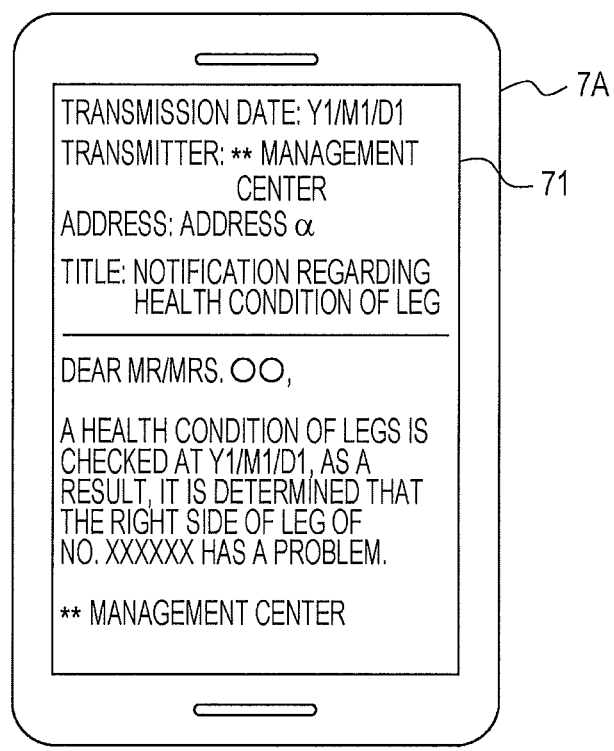
FIG. 8 is a schematic diagram illustrating an example of a notification screen when there is a problem in the health condition of the leg.

FIG. 8 is a schematic diagram illustrating an example of a notification screen in a case in which the health condition of the leg is problematic. When the notification message generated in Step S6 is transmitted as an e-mail, the notification message may be read using the general communication terminal such as the smart phone. When the notification message is an e-mail, as illustrated in FIG. 8, in a screen 71 of the terminal 7A, a date when the health condition of the leg is checked, a name of the horse having the problem in the leg, and a message to be transmitted which indicates the problem occurs in the leg are displayed. For this reason, for example, when a mail address used by a veterinarian or a trainer is registered in the notification destination address of the medical chart, it may be recognized early that the problem has occurred in the leg. In addition, since the veterinarian or the trainer also recognizes which leg has the problem, the veterinarian or the trainer may respond to or treat the problem in advance. Problem detection may be further transmitted explicitly to people involved by combining a vibration function of the terminal 7A. For example, the terminal that a rider has is made to vibrate, such that training is stopped and the veterinarian may check the horse.

When notifying the determination result, the determination result is written into the medical chart DB (Step S7), and the determination process of the health condition is terminated. In Step S7, as described above, the column of the determination date and the determination result of the medical chart number corresponding to the sensor set ID obtained in Step S1 are updated. In addition, when writing the determination date and the determination result into the medical chart DB 23, for example, the determination results obtained over several recent weeks to several months may be accumulated.

Next, the determination method in the cause determination process (Step S5) described above will be described in detail with reference to specific examples.

FIG. 9 is a graph describing a specific example of the determination method of the leg having the problem in the health condition in the first embodiment.

In the cause determination process of the embodiment, in comparison with each data of the vertical direction component of the acceleration (vertical acceleration) of the right front leg, the left front leg, and the neck to each other, it is determined that the cause of the problem occurred in the balance between the right and the left sides exists in any one of the right front leg, the left front leg, and either of the hind legs. When the problem of inflammation, or the like occurs in the left front leg, each vertical acceleration of the right front leg, the left front leg, and the neck is distributed, for example, as illustrated in FIG. 9. Moreover, FIG. 9 illustrates each of the vertical accelerations measured in a state in which only the left front leg has the problem and the right front leg and the hind legs do not have the problem.

The timing when the right front leg is grounded in the vertical acceleration data of the right front leg corresponds to a timing of a peak synchronized with a downwardly convex peak in the vertical acceleration of the neck among the downwardly convex peaks. Accordingly, in the graph illustrated in FIG. 9, the times t1, t3, and t5 (t1<t3<t5) are grounding timings of the right front leg.

In the same manner, the timing when the left front leg is grounded in the vertical acceleration data of the left front leg is a peak synchronized with the downwardly convex peak in the vertical acceleration of the neck among the downwardly convex peaks. Accordingly, in the graph illustrated in FIG.

9, the time t2 (t1<t2<t3) and the time t4 (t3<t4<t5) are grounding timings of the left front leg.

In Step S501 of the cause determination process, the following (1) and (2) are investigated.

(1) The difference ΔP1 between the value P11 of the peak of the acceleration in the upward direction (upwardly convex peak) of the right front leg which appears immediately after the timing when the right front leg is grounded and the value P12 of the peak of the acceleration in the upward direction of the neck.

(2) The difference ΔP2 between the value 21 of the peak of the acceleration in the upward direction of the left front leg which appears immediately after the timing when the left front leg is grounded and the value P22 of the peak of the acceleration in the upward direction of the neck.

Moreover, the period of time immediately after the timing when the right front leg is grounded is in a period from being grounded of the right front leg as described above to initially being grounded of the left front leg, and corresponds to a period ΔT1 illustrated in FIG. 9. That is, the above described (1) means that the difference ΔP1 between the value P11 of the peak of the acceleration in the upward direction of the right front leg that appears in the period ΔT1 illustrated in FIG. 9 and the value P12 of the peak of the acceleration in the upward direction of the neck is investigated. In the same manner, the above described (2) means that the difference ΔP2 between the value P21 of the peak of the acceleration in the upward direction of the left front leg that appears immediately after the timing, which appears in a period ΔT2 illustrated in FIG. 9 when the left front leg is grounded and the value P22 of the peak of the acceleration in the upward direction of the neck is investigated.

Incidentally, concerning a trained horse, such as the racehorse, the neck of the horse does not upwardly move significantly at a normal time, when the leg does not have the problem of inflammation, or the like. Particularly, vertical movement of the neck during running does not occur in "walking" or "trotting". In addition, even in "cantering" or "galloping", the neck moves downwardly according to a running rhythm; however, the horse is trained so as not to raise its neck. That is, a main cause of a change in the vertical acceleration of the neck when the leg does not have the problem of inflammation, or the like is a movement (changing of position) in the vertical direction of the horse's body during running. For this reason, when the leg does not have the problem, as the peaks of the acceleration in the upward direction of the right front leg and the neck that appears in the period ΔT1 illustrated FIG. 9, the difference ΔP1 between both values of the peaks decreases.

Meanwhile, when the front leg has the problem of inflammation, or the like, since the horse feels pain when the leg is grounded, the weight shifts to its hind legs when the leg is grounded so as to reduce the impact (pain) at the time of being grounded. At this time, the horse shifts its weight to its hind legs by moving its neck in an upward direction (tilting its neck back). That is, the change of the vertical acceleration of the neck, immediately after the grounding of the leg having the problem is caused by both the movement (changing of position) in the upward direction of the horse body during running and movement of the neck in the upward direction. For this reason, when the leg having the problem is grounded, the difference ΔP2 between both values of the peaks increases as the peaks of the acceleration in the upward direction of the left front leg and the neck which appears in the period ΔT2 illustrated in FIG. 9.

Accordingly, based on the difference ΔP between the peaks of the acceleration in the upward direction of the right front leg and the neck in the period ΔT from being grounded of one front leg (for example, right front leg) to being grounded of the other front leg (for example, left front leg), it is determined whether or not the right front leg has the problem.

Moreover, whether or not the front leg has the problem is not limited to the difference ΔP of the above described peaks, and may be determined, for example, based on a proportion of the peaks of the acceleration in the upward direction (upwardly convex peak) of the front leg and the neck. That is, whether or not the front leg has the problem may be determined depending on whether or not P1 in (A) and P2 in (B) are equal to or more than the threshold.

(A) A proportion P1 (=P12/P11) of the value P11 of the peak of the acceleration in the upward direction of the right front leg (upwardly convex peak) which appears immediately after the timing when the right front leg is grounded and the value P12 of the peak of the acceleration in the upward direction of the neck.

(B) A proportion P2 (=P22/P21) of the value P21 of the peak of the acceleration in the upward direction of the left front leg which appears immediately after the timing when the left front leg is grounded and the value P22 of the peak of the acceleration in the upward direction of the neck.

When determining which leg has a problem, based on the above described proportions P1 and P2, the threshold in Step S502 is set to a value between about 1.3 to 2, for example.

As described above, in the determination method of the health condition of the leg of the horse according to the first embodiment, whether or not there is a problem with any of the right front leg, the left front leg, and the hind legs is determined by using a unique motion that the weight shifts to its hind legs when the leg is grounded, which is made when the problem of inflammation, or the like is caused in the front leg. For this reason, an early mild inflammation, and the like, even when a determination by only a visual inspection or a palpation is difficult, the leg having the problem may be narrowed down, such that the time taken and effort spent for a medical examination may be reduced. In addition, a stress given to the horse due to the medical examination may be reduced.

In addition, since the vertical acceleration data of the right front leg and the left front leg are separately obtained and compared with the vertical acceleration data of the neck, it may be determined directly from the compared result that the problem occurs in the right front leg or the left front leg. For this reason, regardless of the way the horse moves its legs, for example, horse gaits or, which one of the right front leg and the left front leg is leading, or the like, it may be determined that the problem occurs in the right front leg or the left front leg. Accordingly, since the data in regard to the moving of the leg in the normal state or the like do not have to be measured in advance, the time and effort for obtaining the data in the normal state is reduced. Moreover, the above described the "leading" in regard to the gait of the horse indicates a leg positioned on the front side of the horse body side, in a positional relationship in a front-back direction of the horse body of a right side leg and a left side leg of the horse during running. For example, when the right side of leg is positioned on the front side of the horse body further than the left side of leg, it is indicated that a right front leg is leading.

In addition, as exemplified in the embodiment, the first sensor 5A and the second sensor 5B which detect the grounding timing of the right front leg and the left front leg may be mounted in the abdomen of the horse using the surcingle 91. For this reason, injury in the front leg or a breakdown of the sensor when the horse bumps its front leg (sensor) against a bar or a wall, or an injury in the hind leg caused when the hind leg steps on a sensor detached during running, all of which may be caused when the sensor is mounted on the front leg, may be suppressed. Therefore, the safety is improved in comparison with a case in which the sensor is mounted on the front leg.

Further, regarding a graph illustrated in FIG. 9, it will be described below. For example, in the timing when the right front leg having no problem is grounded like a time t5, the peak value of the vertical acceleration of the neck is smaller than the peak value of the vertical acceleration of the right front leg. Meanwhile, like a time t4, in the timing when the left front leg having the problem is grounded, the peak value of the vertical acceleration of the neck is greater than the peak value of the vertical acceleration of the left front leg. The difference is also related to moving of the neck for alleviating a pain (impact) when the left front leg is grounded. In the timing when the left front leg having the problem is grounded, the neck is moved upwardly while the position of the horse body is moved downward and the weight shifts to the hind legs side. That is, in the timing when the leg having the problem is grounded, since only the neck is only moved upwardly before a position of vertical direction of the neck is fallen to a position in the normal state, the value of the downwardly convex peak of the vertical acceleration becomes great. Accordingly, based on a relationship between the difference ΔP3 of the downwardly convex peak values of the vertical acceleration of the right front leg and the neck in the timing when the right front leg is grounded and the difference ΔP4 of the downwardly convex peak values of the vertical acceleration of the left front leg and the neck in the timing when the left front leg is grounded, the front leg in which the problem occurs may be determined.

In addition, by combining a relationship of the values of the upwardly convex peaks of the vertical accelerations immediately after the timing when the front leg is grounded with a relationship of the values of the upwardly convex peaks of the vertical accelerations in timing when the front leg is grounded, it is thought that a determination accuracy of the front leg having the problem may be improved.

In the meantime, the health condition management apparatus 2 that performs the determination method of the health condition of the leg, for example, is realized by a computer and a program which causes the computer to execute each of the processes in the determination method described above. A hardware configuration of the health condition management apparatus 2 realized by the computer and the program will be simply described with reference to FIG. 10.

FIG. 10 is a schematic diagram illustrating a hardware configuration of the health condition management apparatus. As illustrated in FIG. 10, a computer 10 includes a central processing unit (CPU) 1001, a memory 1002, a hard disk drive (HDD) 1003, an input device 1004, a display device 1005, an interface 1006, and a medium driving device 1007. Any two of the CPU 1001, the memory 1002, the HDD 1003, the input device 1004, the display device 1005, the interface 1006, and the medium driving device 1007 may transmit data therebetween through a bus 1008.

The CPU 1001 is an operation processing device which controls the entire operations of the computer 10 by executing various programs.

The memory 1002 is a semiconductor memory such as a read-only memory (ROM) or a random access memory (RAM). In the ROM, for example, a predetermined basic control program read by the CPU 1001 is recorded in advance at the time of operating the computer 10. In addition, the RAM is used as a working storage area as occasion calls when the CPU 1001 executes various programs.

The HDD 1003 is an auxiliary storage device that stores various programs executed by the CPU 1001 or various data including the medical chart DB 23. The CPU 1001 executes a process for determining the health condition of the leg or management of the medical chart DB 23 by reading and executing the program stored in the HDD 1003.

The input device 1004, for example, is a keyboard or a mouse. When the input device 1004 is operated by an operator (user) of the computer 10, input information corresponding to operation contents is transmitted to the CPU 1001.

The display device 1005, for example, is a liquid crystal display, and displays various texts or images including the medical chart DB 23 in response to display data received from the CPU 1001.

The interface 1006 is communicably coupled to the computer 10 and the network 4, and executes obtaining the acceleration data from the sensor sets 5, transmitting the notification message, and the like.

The medium driving device 1007 is a device that executes reading various program or data stored in a portable recording medium 11. The CPU 1001 reads a predetermined program stored in the portable recording medium 11 through the medium driving device 1007, such that the above described determination process may be executed. Moreover, as the portable recording medium 11, for example, there is a storage device including a connector with standards such as a compact disc read-only memory (CD-ROM), a digital versatile disc read-only memory (DVD-ROM), or a Universal Serial Bus (USB).

The CPU 1001, the memory 1002, the HDD 1003, the interface 1006, and the medium driving device 1007 cooperate and perform processing in accordance with the above described flow chart, such that the computer 10 realizes each function of the health condition management apparatus 2 illustrated in FIG. 2.

As described above, according to the determination method of the health condition of the leg of the horse according to the first embodiment, which one of the right front leg, the left front leg, and the hind legs has the problem is determined by the health condition management apparatus 2 (computer), the effort spent or the time taken for specifying the leg having the problem may be reduced. In addition, since the leg having the problem is specified (determined) using the vertical direction component (vertical acceleration data) of the acceleration data of three parts such as the right front leg, the left front leg, and the neck and a specific movement of the horse with its leg having the problem, the data of the normal state does not have to be obtained in advance. For this reason, specifying which leg of the horse has the problem such as a disease or injury may be supported by a simple method.

Further, in the determination method of the embodiment, the first sensor 5A and the second sensor 5B are used to measure the acceleration data of the right front leg and the left front leg, respectively. The first and second sensors 5A and 5B are mounted to the right side of the abdomen and the left side of the abdomen, respectively, or the right side of the chest and the left side of the chest, respectively. When the first and second sensors 5A and 5B are mounted on the right side of the abdomen and the left side of the abdomen, the surcingle 91 may be used. When the first and second sensors 5A and 5B are mounted on the right side of the chest and the left side of the chest, the breast collar 92 may be used. The surcingle 91 or the breast collar 92 is a horse harness (auxiliary tool) which is used at the time of fixing the position of a saddle with which the racehorse habitually wears. For this reason, compared to a case in which the first sensor 5A and the second sensor 5B are mounted on the front leg, the discomfort to the horse may be reduced. In the same manner, even when the third sensor 5C used in the data of the acceleration of the neck is attached to the chest, the neck, the head, or the like, the horse harness (auxiliary tool) which is used habitually on a racehorse may be used. For this reason, the discomfort due to mounting of the third sensor 5C may also be reduced. Beside, as described above, safety is improved compared to a case in which the sensor is mounted on the leg.

Moreover, a configuration of the health condition management system 1 including the health condition management apparatus 2 according to the embodiment may be suitably changed. For example, the first access point 3A illustrated in FIG. 1 and FIG. 2 may be a terminal such as a personal computer which is communicably coupled to the network 4. When the terminal is used as the first access point 3A, for example, the terminal and the first sensor 5A to the third sensor 5C are connected to each other using a Universal Serial Bus (USB), and the acceleration data of each of the sensors 5A to 5C may be transmitted to the health condition management apparatus 2.

In addition, when determining that the leg has the problem, not only the notification message is transmitted, and for example, but the notification message may also be displayed on the display device such as the liquid crystal display installed in the training facilities 6.

Further, one of the sensor sets 5, for example, may be configured to include one communication control apparatus which is connected to the first sensor 5A to the third sensor 5C.

Second Embodiment

In the first embodiment, the vertical acceleration of the right front leg is measured by the first sensor 5A, and the vertical acceleration of the left front leg is measured by the second sensor 5B. However, the vertical acceleration of both front legs is not limited thereto, and may be measured and obtained by other methods. In the embodiment, other examples of a combination of the vertical acceleration measured by the sensor sets 5 and the determination method of the leg having the problem will be described.

Figure 12:
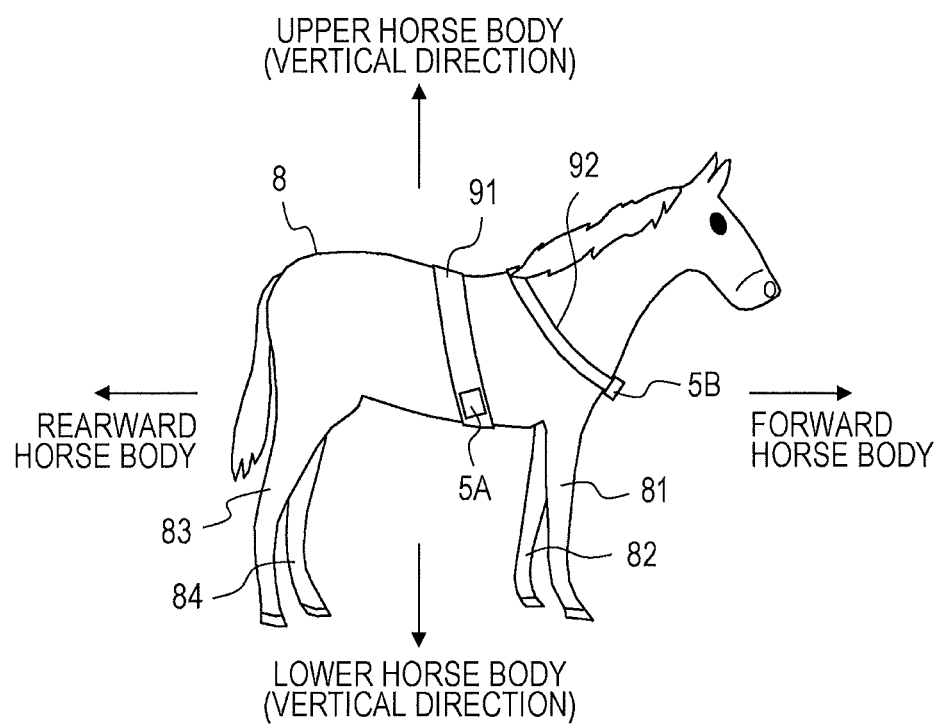
FIG. 12 is a schematic diagram illustrating an attaching method of a first sensor and a second sensor in the determination method according to the second embodiment.

FIG. 11 is a diagram illustrating an object, or the like of obtaining data of a first sensor and a second sensor in the determination method of the health condition of the leg of the horse according to the second embodiment of the embodiment. FIG. 12 is a schematic diagram illustrating an attaching method of the first sensor and the second sensor to the horse body in the determination method according to the second embodiment.

In the determination method of the health condition of the horse of the embodiment, as illustrated in FIG. 11, the grounding timing of the right front leg and the left front leg is detected and specified based on the measurement value of the first sensor 5A. For this reason, in the embodiment, the vertical direction component of the acceleration (vertical acceleration) of one front leg is obtained from the first sensor 5A, as illustrated in FIG. 11. In addition, the second sensor 5B obtains, as illustrated in FIG. 11, data for detecting the timing of the weight-shift to the rear side of the horse body. Even in the embodiment, similar to the first embodiment, the timing of the weight-shift is detected from the time change of the vertical movement of the neck (moving of the horse body in the vertical direction). For this reason, the second sensor obtains the vertical direction component of the acceleration of the neck.

In addition, even in the embodiment, as illustrated in FIG. 12, the vertically upward side and the vertically downward side in a state in which the horse 8 stands on its four legs 81 to 84 are respectively referred to as the upper side of the horse body and the lower side of the horse body. In addition, the direction of the hind legs 83 and 84 when viewed from the front legs 81 and 82 is referred to as the rear side of the horse body, and the direction opposite to the direction of the hind legs 83 and 84 when viewed from the front legs 81 and 82 is referred to as the front side of the horse body. Further, a right side and left side of the horse when seeing the front side of the horse body from the horse body in the state in which the horse 8 stands on its four legs 81 to 84 are respectively referred to as the right horse body and the left horse body.

The first sensor 5A that measures the acceleration of the front leg is mounted on a region associated with the vertical movement of the front leg 81 or 82 in the horse 8, for example, as illustrated in FIG. 12, the right side of the abdomen. In addition, the second sensor 5B that measures the acceleration of the neck is mounted on a region associated with the vertical movement of the neck in the horse 8, for example, the neck, the chest, or the head. In the embodiment, similar to the first embodiment, the second sensor 5B is mounted on the chest.

When the first sensor 5A is mounted on the abdomen, as illustrated in FIG. 12, the first sensor 5A is attached to the surcingle 91. When the second sensor 5B is mounted on the chest, as illustrated in FIG. 12, the second sensor 5B is mounted on the chest using the breast collar 92. Accordingly, as described in the first embodiment, the discomfort to the horse due to mounting of the first sensor 5A and the second sensor 5B may be reduced. In addition, safety is improved in comparison with a case in which the sensor is mounted on the leg.

As described above, the first sensor 5A and the second sensor 5B measure vertical acceleration. For this reason, even in the embodiment, as the first sensor 5A and the second sensor 5B, the acceleration sensor is used. The measurement value (acceleration data) of the first sensor 5A and the second sensor 5B may be transmitted, separately for each sensor, to the health condition management apparatus 2, or may be transmitted to the health condition management apparatus 2 using one communication apparatus connected to the first sensor 5A and the second sensor 5B.

In addition, the first sensor 5A and the second sensor 5B, for example, may transmit the measurement value to the health condition management apparatus 2 whenever the measurement value is output, or the measurement value within a certain period (for example, a few minutes to several tens of minutes) may be accumulated in the sensor and transmitted to the health condition management apparatus 2.

The determination process of the health condition of the leg of the horse in the health condition management apparatus of the embodiment is executed according to the flow chart illustrated in FIG. 6. However, since the first embodiment and the second embodiment have different data obtained in Step S1 from each of the sensor sets 5, the contents of the cause determination process of Step S5 illustrated in FIG. 6 is different from the first embodiment.

Hereinafter, the cause determination process among the determination methods of the health condition of the leg of the horse in the health condition management apparatus of the embodiment will be described with reference to FIG. 13 to FIG. 15.

Figure 13:
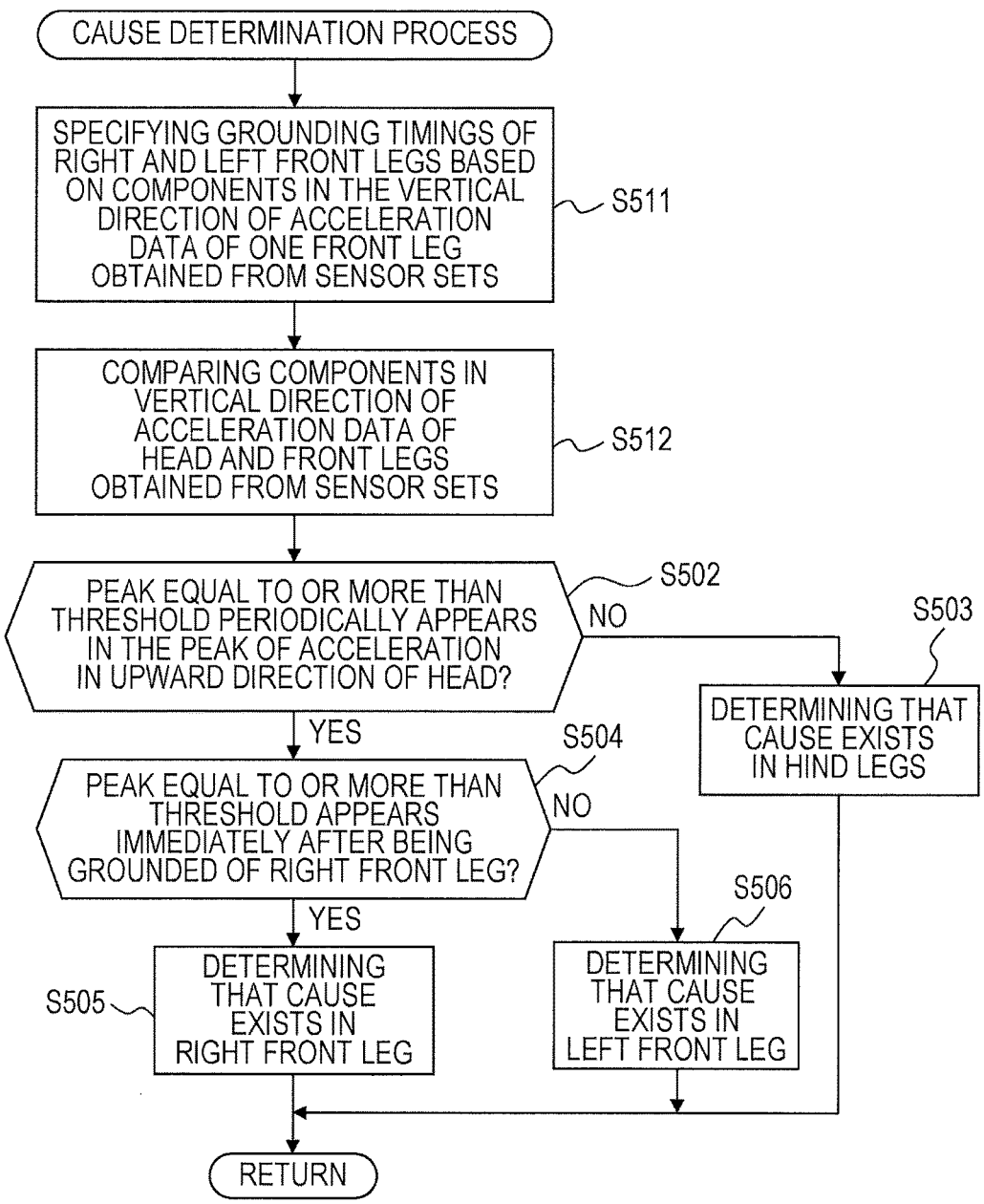
FIG. 13 is a flow chart illustrating contents of a cause determination process in the determination method according to the second embodiment.

FIG. 13 is a flow chart illustrating the contents of the cause determination process in the determination method according to the second embodiment. FIGS. 14A to 14G are schematic diagrams of the gait of a horse at the time of trotting. FIG. 15 is a graph describing a specifying method of the grounding timing of the right front leg and the left front leg.

The cause determination process in the determination method of the embodiment is performed, similar to the first embodiment, when a problem occurs in the balance between the right and the left sides. In the cause determination process of the embodiment, as illustrated in FIG. 13, first, based on the vertical direction component of the acceleration data of one front leg (a front leg to which the sensor sets are attached) obtained from the sensor sets 5, the grounding timings of the right front leg and the left front leg are specified (Step S511). A process of Step S511 is performed by the data comparison unit 22B of the leg condition determination unit 22 (referring to FIG. 2). The data comparison unit 22B specifies a period of time when the one front leg is a supporting leg and a period of time when the one front leg is an idling leg, from a waveform between the grounding timings in the acceleration data of one front leg. Moreover, in this specification, the leg supporting a weight of the horse during running is referred to as the supporting leg. In addition, in this specification, a leg which is not the supporting leg in any one of the right and left legs is referred to as the idling leg.

The supporting leg and the idling leg have significantly different waveforms of the vertical acceleration in the period when the leg leaves and then is grounded. For this reason, when either leg of the right or left leg is recognized as the supporting leg, the grounding timings of the right front leg and the left front leg in the vertical acceleration data may be specified. A specifying method of the grounding timing of the right front leg and the left front leg will be simply described with reference to FIG. 14A to FIG. 15.

Figure 14A:
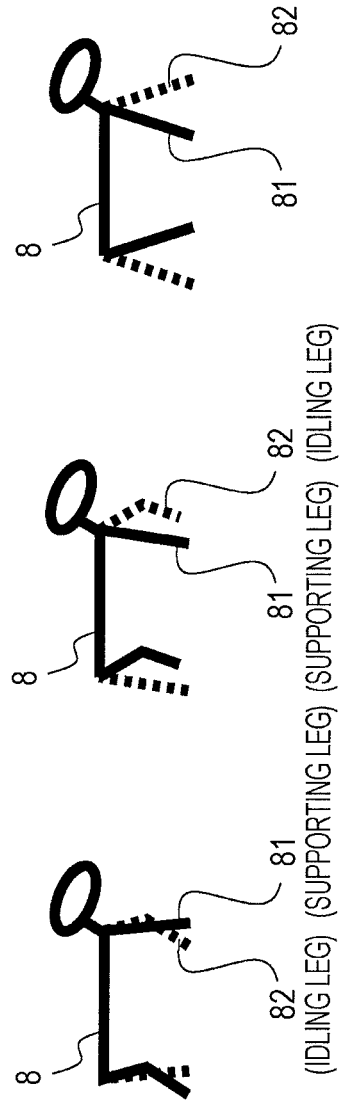
FIGS. 14A to 14G are schematic diagrams of a gait of the horse at the time of trotting.
Figure 14B:
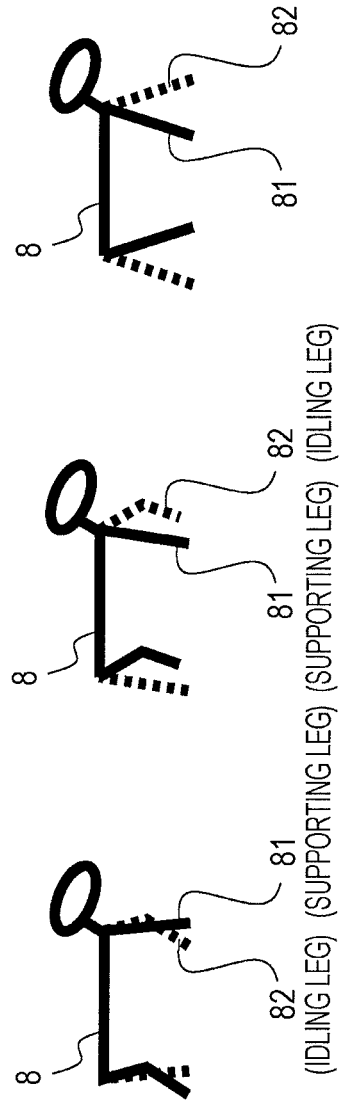
Figure 14C:
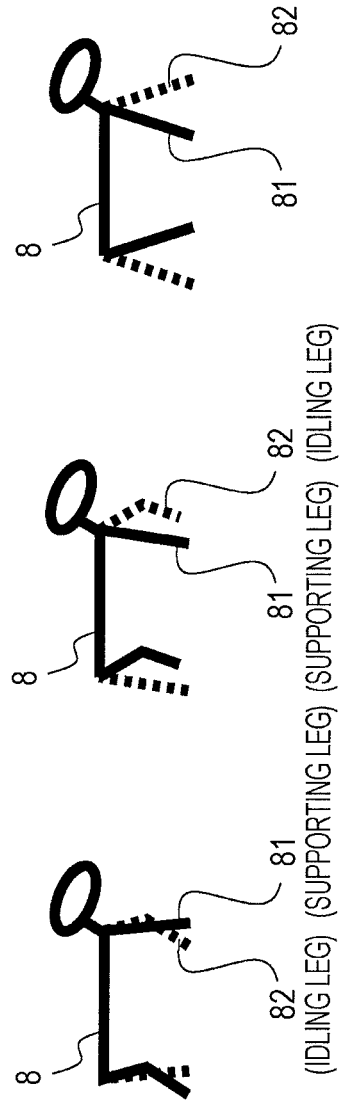
Figure 14D:
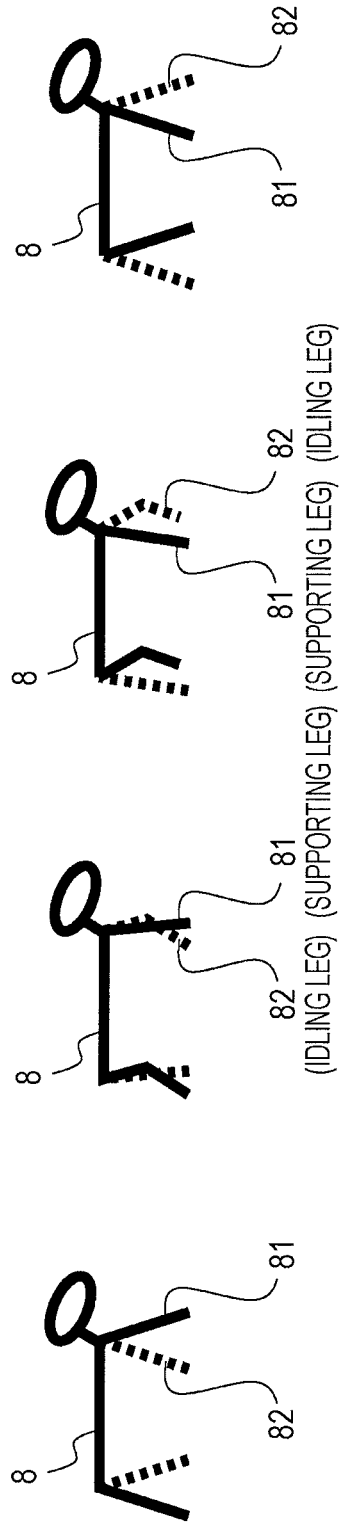
Figure 14E:
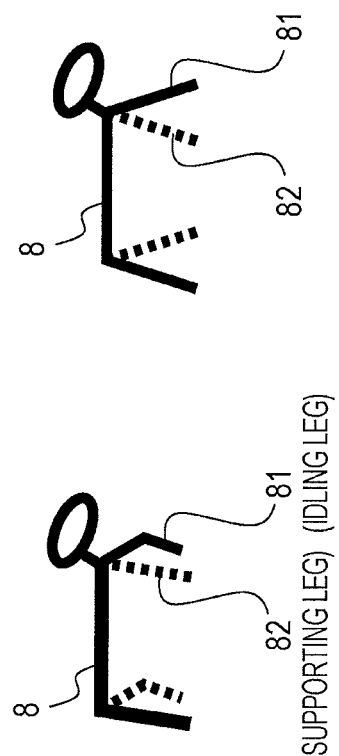
Figure 14F:
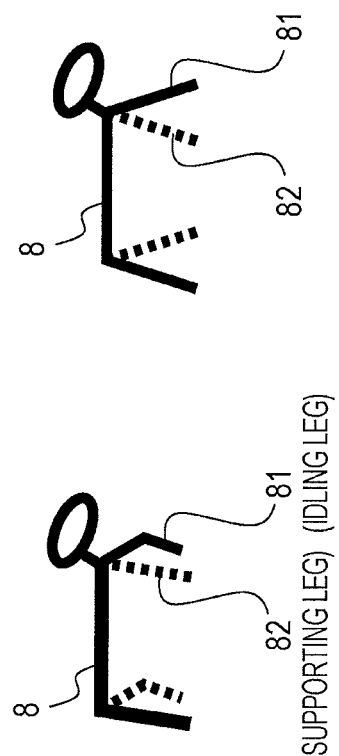
Figure 14G:
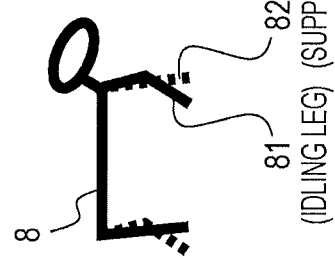

When focusing on the one leg of the gait of the horse during trotting, as illustrated in FIGS. 14A to 14G, the supporting leg and the idling leg are alternately repeated. As illustrated in FIGS. 14A to 14C, the horse 8 moves forward when the right front leg 81 is grounded and then the left front leg 82 is raised. At this time, since the right front leg 81 supports the weight, the right front leg 81 is the supporting leg, and the left front leg 82 is the idling leg. After that, when the left front leg 82 is grounded (FIG. 14D), as illustrated in FIGS. 14E and 14F, in this period of time, the right front leg 81 is raised so that the horse moves forward. At this time, since the left front leg 82 supports the weight, the right front leg 81 is the idling leg, and the left front leg 82 is the supporting leg. Therefore, when the right front leg 81 is grounded (FIG. 14G), the state of the horse returns to a state illustrated in FIG. 14A, and then, the motions of FIGS. 14A to 14F are repeated. For this reason, data of the first sensor 5A relating to the moving of the one side front leg during trotting, as illustrated in FIG. 15, waveform of having one upwardly convex peak and waveform of two upwardly convex peaks are repeated. As the periods ΔT1, ΔT3, and ΔT5 illustrated in FIG. 15, the waveform of one upwardly convex peak indicates the supporting leg supporting the weight, that is, a state in which the weight shifts while the leg of the horse is grounded is illustrated. As the period ΔT2 and ΔT4 illustrated in FIG. 15, the waveform of two upwardly convex peaks indicates a state in which the corresponding leg is moved forward while supporting by the opposite leg, that is, the corresponding leg is the idling leg. The idling leg is accompanied by a motion in which the leg is straight at the time of being grounded after kicking the ground and raising the leg. For this reason, the waveform of the vertical acceleration of the front leg in the period in which the idling leg leaves the ground and is grounded again is the waveform of two upwardly convex peaks. That is, among downwardly convex peaks in the waveform illustrated in FIG. 15, the downwardly convex peak when the period of the waveform of two downwardly convex peaks is finished indicates the grounding timing of the front leg (right front leg 81 in the embodiment) in which acceleration is measured. In addition, since the downwardly convex peak at the end of the period of the waveform of one convex peak indicates the timing when the front leg, at the side in which acceleration is measured, is raised, the other front leg of the front legs (left front leg 82 in the embodiment) is grounded immediately after the timing. Therefore, the grounding timing of the right front leg and the left front leg may be specified from the vertical direction components of the acceleration illustrated in FIG. 15.

When the data of the first sensor 5A relating to moving of the one side front leg and the data of the second sensor 5B relating to moving of the neck are synchronized and the neck is significantly moved when the front leg is the supporting leg which is determined by the waveform properties described above, the front leg in which the first sensor 5A is mounted has a problem. When the neck is significantly moved when the front leg is the idling leg, it is determined that the front leg opposite to the leg in which the first sensor 5A is mounted has a problem.

Returning to the flow chart of FIG. 13, when specifying the grounding timing of the right front leg and the left front leg, the vertical direction components of the acceleration data of the neck and the front leg are compared to each other (Step S512). The process of Step S512 is performed by the data comparison unit 22B. The data comparison unit 22B performs the same comparison as the process of Step S501 in the first embodiment, and investigates the differences ΔP1 and ΔP2 of the peak values of (1) and (2) or the proportions P1 and P2 of the peak values of (A) and (B) described above.

Two sets of vertical acceleration data are compared to each other and the differences ΔP1 and ΔP2 of the peak values or the proportion P1 and P2 of the peak values are investigated, and then it is determined that the peaks equal to or more than the threshold periodically appears in the peak of the acceleration in the upward direction of the neck (Step S502). A process of Step S502 is performed by the leg specifying unit 22C. The leg specifying unit 22C performs the process as described in the first embodiment. In addition, when determining based on the proportion P1 and P2 of the peak values, for example, a value 1.5 to 2 times more than a value of the upwardly convex peak in the vertical acceleration of the front leg is a threshold.

When the peak equal to or more than the threshold is not periodically appears (No in Step S502), the leg specifying unit 22C determines that the cause of the problem that occurs in the balance between the right and the left sides is in the hind legs (Step S503), and then the cause determination process is terminated in which the process is shifted to "return".

Meanwhile, when the peak equal to or more than the threshold periodically appears (Yes in Step S502), the leg specifying unit 22C determines whether or not the peak equal to or more than the threshold appears immediately after the right front leg is grounded (Step S504). In Step S504, depending on whether or not the front leg that is grounded immediately before the timing when the peak equal to or more than the threshold appears is the right front leg, it is determined whether or not the timing when the peak equal to or more than the threshold appears is immediately after the right front leg is grounded. When the peak equal to or more than the threshold appears immediately after the right front leg is grounded (Yes in Step S504), the leg specifying unit 22C determines that the cause of the problem that occurs in the balance between the right and the left sides is in the right front leg (Step S505), and then the cause determination process is terminated in which the process is shifted to "return". In addition, when the peak equal to or more than the threshold does not appears immediately after the right front leg is grounded (No in Step S504), the leg specifying unit 22C determines that the cause is in the left front leg (Step S506), and then the cause determination process is terminated in which the process is shifted to "return".

When the cause determination process is terminated, the determination result is notified to a predetermined terminal (Step S6) and is written into the medical chart DB 23 (Step S7), as illustrated in FIG. 6.

Next, the determination method of the cause determination process of the embodiment will be described in detail with specific examples.

Figure 16:
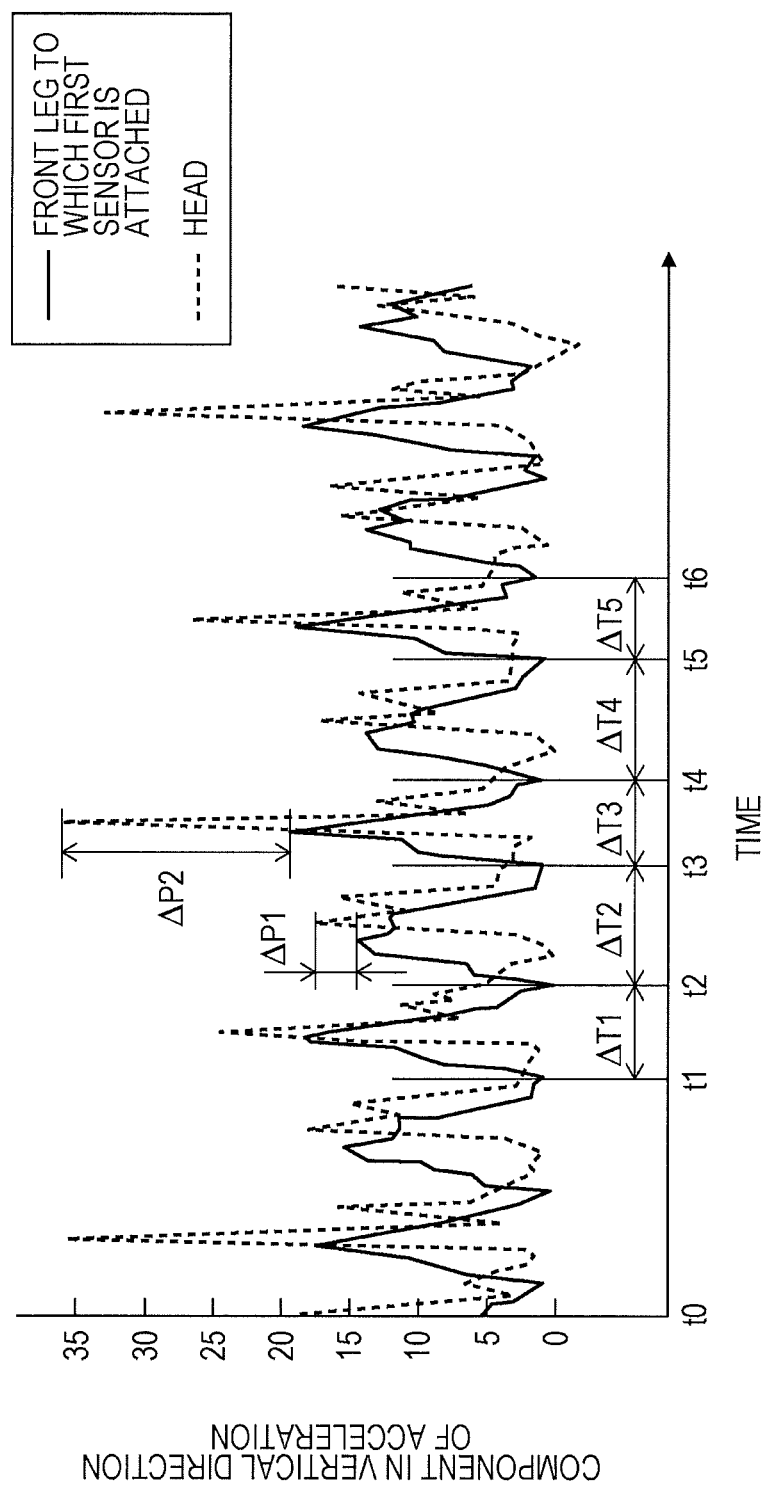
FIG. 16 is a graph describing a specific example of a determination method of the leg having a problem in the health condition in the second embodiment.

FIG. 16 is a graph describing a specific example of the determination method of the leg in which a problem occurs in the health condition in the second embodiment.

The vertical direction component (the vertical acceleration data) of the acceleration data of the front leg, for example, is described in a graph as illustrated FIG. 15. In such a vertical acceleration data of the front leg, the downwardly convex peak corresponds to each grounding timing of the legs. In addition, in the vertical acceleration data of the front leg, the grounding timing of the right front leg and the grounding timing of the left front leg appear alternately. When the sensor 5A is attached to right side of the horse body, in a graph illustrated in FIGS. 14A to 14G, as described above, the times t1, t3, and t5 are the grounding timing of the right front leg, and the times t2, t4, and t6 or the times immediately before the times t2, t4, and t6 are the grounding timing of the left front leg.

In the process of Step S512 of the cause determination process of the embodiment, for example, the vertical acceleration data of the neck and the front leg illustrated in FIG. 15 are compared to each other. Moreover, each of times t1 to t6 and periods ΔT1 to ΔT5 in FIG. 15 are the same as the times and the periods illustrated in FIGS. 14A to 14G. In addition, FIG. 15 illustrates that the sensor 5A is attached to the right side of horse body, and the vertical acceleration of the neck illustrated in FIG. 15 is a typical example when a measurement is performed with the horse having the problem in the leg to which the sensor is attached, that is, the right front leg.

As illustrated in FIG. 16, the difference ΔP2 of the upwardly convex peak of the front leg and the neck in the period ΔT3 of the times t3 and t4 is significantly larger than the difference ΔP1 of the upwardly convex peak of the front leg and the neck in the period ΔT2 of the times t2 and t3. As described in the first embodiment, the trained horse such as the racehorse does not move its neck during running at a normal time when the leg does not have the problem of inflammation, or the like. For this reason, at the normal time (leg having no problem), the change of the vertical acceleration of the neck is substantially synchronized with the change of the vertical acceleration of the leg. That is, at the normal time, as the period ΔT2, the difference ΔP1 of the upwardly convex peaks of the neck and the front leg decreases. Since the vertical acceleration of the front leg has two upwardly convex peaks in the period ΔT2, the leg which is grounded at the time t2 when the period ΔT2 is started is the leg opposite to the leg to which the sensor is attached, that is, the left front leg. Therefore, as illustrated in the graph of FIG. 15, it recognizes that the left front leg does not have the problem.

In addition, when the horse feels pain in a case in which the leg having the problem is grounded, the horse moves the neck upwardly so that the weight moves to the rear side. For this reason, as the period ΔT3, the upwardly convex peak of the vertical acceleration of the neck becomes significantly large between the grounding timing of the one leg and the grounding timing of the leg of the other leg. Accordingly, when the front leg has a problem when starting the period, the difference ΔP2 of the upwardly convex peaks of the front leg and the neck becomes significant. That is, when the difference of the upwardly convex peaks of the front leg and the neck is great, it is determined that the leg which is grounded at the time of starting the period has the problem. In an example illustrated in FIG. 15, since the vertical acceleration of the front leg in the period ΔT3 has single upwardly convex peak, the leg which is grounded at the time t3 when the period ΔT3 is started is the front leg to which the sensor is attached, that is, the right front leg. Therefore, it may be determined that the right front leg has the problem from the graph illustrated in FIG. 15.

Even in the determination method of the health condition of the leg of the horse according to the second embodiment, using a unique motion in which the horse moves the weight to the hind legs side when the leg is grounded in a case in which the problem of inflammation, or the like occurs in the front leg of the horse, it is determined whether or not any of right front leg, the left front leg, and the hind legs has the problem. For this reason, an early mild inflammation, and the like, even when a determination by only a visual inspection or a palpation is difficult, the leg having the problem may be narrowed down, such that the time and effort spent for a medical examination may be reduced. In addition, a stress given to the horse due to the medical examination may be reduced.

As described above, in accordance with the determination method of the health condition of the leg of the horse according to the second embodiment, since whether or not any of the right front leg, the left front leg, and the hind legs has the problem is determined by the health condition management apparatus 2 (computer), the effort spent or time taken for specifying the leg having the problem may be reduced. In addition, since the leg having the problem is specified (determined) using a unique motion of the horse in which a leg has a problem, such as that the neck is significantly moved upwardly when the leg having the problem is grounded, the data in the normal state do not have to be obtained in advance. For this reason, specifying which leg of the horse has the problem may be supported by a simple method.

Further, in the determination method of the embodiment, the first sensor 5A to the third sensor 5C, which is used to measure the acceleration data, are attached to the horse harness (auxiliary tool) which is used at the time of fixing the position of the saddle, such as the surcingle 91 or the breast collar 92. Since the surcingle 91 or the breast collar 92 is habitually mounted on the racehorse, discomfort due to the mounting of the first sensor 5A to the third sensor 5C may be reduced.

Third Embodiment

In the first and second embodiments, the grounding timings of the right front leg and the left front leg are detected using the acceleration sensors. However, a determination of the leg grounded is not limited thereto, and may also be measured and obtained by other methods. In a third embodiment, the determination method of the leg having the problem will be described using angular velocity data in addition to information measured by the sensor sets 5.

Figure 18:
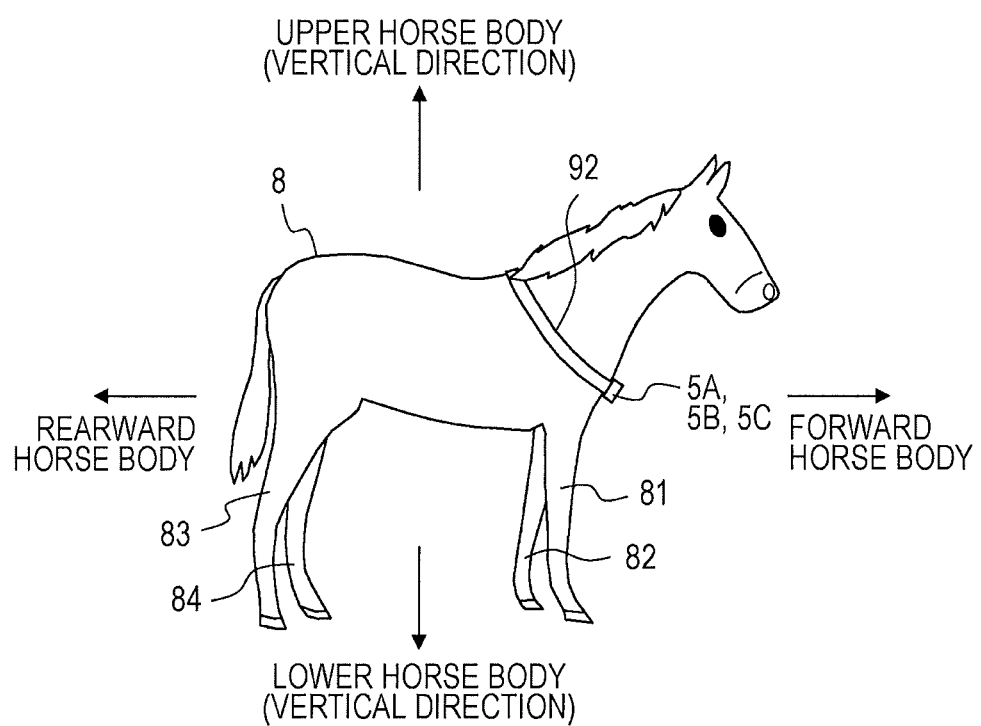
FIG. 18 is a schematic diagram illustrating a method of attaching the first sensor to the third sensor to the horse body according to the third embodiment.

FIG. 17 is a diagram describing an object, or the like of obtaining data of the first sensor to the third sensor in the determination method of the health condition of the leg of the horse according to the third embodiment. FIG. 18 is a schematic diagram illustrating an attaching method of the first sensor to the third sensor to the horse body in the determination method according to the third embodiment. FIGS. 19A1 to 19C2 are schematic diagrams describing a relationship between the gait of the horse and a rotation of the chest in a yaw-axis direction.

In the determination method of the health condition of the horse of the embodiment, as illustrated in FIG. 17, the grounding timings of the right front leg and the left front leg are detected based on the measurement value of the first sensor 5A. For this reason, as illustrated in FIG. 17, the first sensor 5A obtains the vertical direction component of the acceleration (vertical acceleration) of the chest position. The second sensor 5B obtains, as illustrated in FIG. 17, a yaw-axis component of the angular velocity of the chest position, and specifies the grounding timings of the right front leg and the left front leg. The third sensor 5C obtains, as illustrated in FIG. 17, data for detecting the timing of the weight-shift to the rear side of the horse body. Even in the embodiment, like the first embodiment, the timing of the weight-shift is detected from the time change of the vertical movement of the neck (moving of the horse body in the vertical direction). For this reason, the third sensor obtains the vertical direction component of the acceleration of the neck.

In addition, even in the embodiment, as illustrated in FIG. 18, the vertically upward direction and the vertically downward direction when the horse 8 stands on its four legs 81 to 84 are respectively referred to as the upper side of the horse body and the lower side of the horse body. In addition, a direction of the hind legs 83 and 84 viewed from the front legs 81 and 82 is referred to as the rear side of the horse body, and a direction opposite to the direction of the hind legs 83 and 84 viewed from the front legs 81 and 82 is referred to as the front side of the horse body. Further, a right side and a left side viewed the front side of the horse body from the horse body standing on the four legs 81 to 84 are respectively referred to as a right horse body and a left horse body. In addition, in the embodiment, as illustrated in FIG. 18, the first sensor 5A to the third sensor 5C are mounted on the breast collar 92.

A difference between the second embodiment and the third embodiment is the specifying method of the grounding timing of the right front leg and the left front leg. In the second embodiment described above, a gait determination is performed by a difference of the waveform of the vertical acceleration, and whether or not leg being grounded is the right front leg or the left front leg is determined. As illustrated in FIGS. 19A1 to 19C2, in the third embodiment, the rotation of the chest 85 in the yaw-axis direction is read, and whether the left or the right leg is about to be moved forward is determined. For example, when the horse 8 moves from the state in which the horse 8 is stopped and both the front legs 81 and 82 are gathered, as illustrated in FIGS. 19A1 and 19A2, to the state in which the left front leg 82 is moved forward, as illustrated in FIGS. 19B1 and 19B2, the angular velocity data of the chest 85 indicates a right rotation in the yaw-axis direction. In a similar manner, the horse 8 moves to the stat in which the right front leg 81 is moved forward as illustrated in FIGS. 19C1 and 19C2, the angular velocity data of the chest 85 indicates a left rotation in the yaw-axis direction. That is, when the angular velocity of the chest 85 is rotated to the left in synchronization with the vertical direction component, the right front leg 81 is the idling leg, and when the angular velocity of the chest 85 is rotated to the right in synchronization with the vertical direction component, the left front leg 82 is the idling leg. Note, FIGS. 19A2, 19B2, and 19C2 are the schematic diagrams of the horse 8 when viewed from the upper side of the horse body. For this reason, the above described left rotation and right rotation is a rotation when viewed from the upper side of the horse body.

Figure 20:
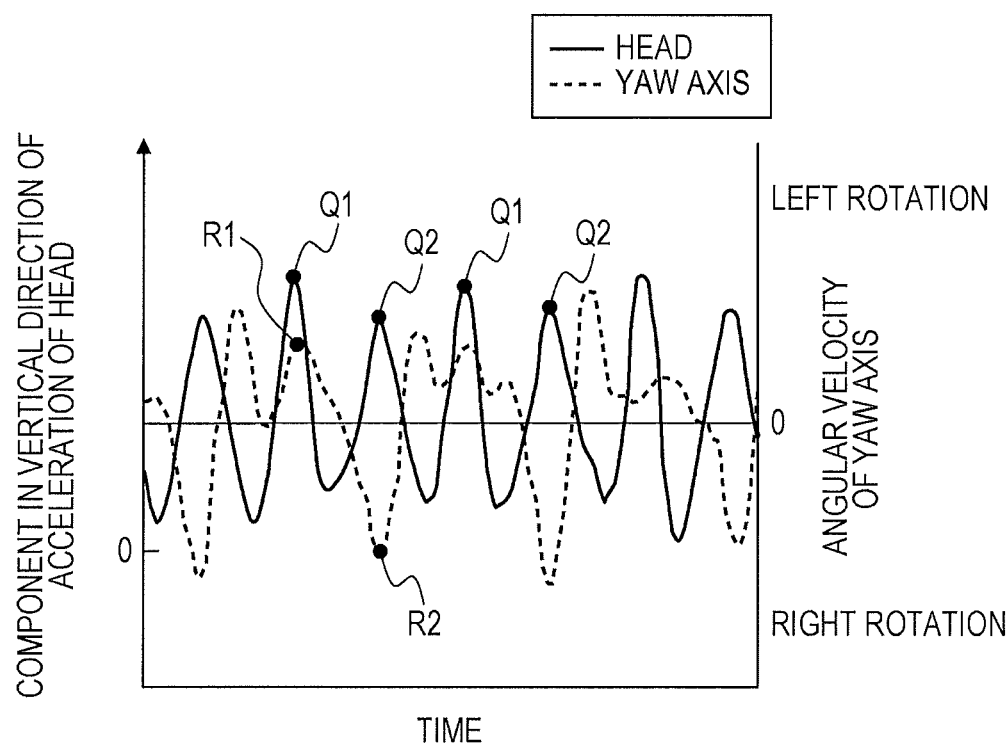
FIG. 20 is a graph illustrating a specific example of a determination method of a leg having a problem in the health condition in the third embodiment.

FIG. 20 is a graph illustrating a specific example of the determination method of the leg having the problem of the health condition in the third embodiment.

As illustrated in FIG. 20, in the upwardly convex peak in the vertical direction component of the acceleration of the neck, a high peak Q1 and a low peak Q2 alternatively appear. When the angular velocity of the yaw axis is overlapped with the vertical direction component of the acceleration of the neck, as illustrated in FIG. 20, the high peak Q1 is synchronized with the upwardly convex peak R1 of the angular velocity in respect to the yaw axis, and the low peak Q2 is assumed to be synchronized with the downwardly convex peak R2 of the angular velocity in respect to the yaw axis. From the graph illustrated in FIG. 20, it may be determined that the neck of the horse 8 is up when the neck rotate in a direction indicated by a plus value of the angular velocity (unit is radian per second) in respect to the yaw axis, that is, a left rotation (rotation to the left). Accordingly, it is recognized that the left leg which is supporting leg has the problem.

Moreover, like the embodiment, when the angular velocity of the chest position and the acceleration of the neck are measured by the acceleration sensor mounted on the chest, both sets of data may be obtained from one sensor. That is, the vertical direction component of the acceleration of the neck may be obtained by extracting from the acceleration data and the angular velocity component of the yaw-axis direction of the chest position may be obtained by extracting from the angular velocity data, and both data are measured by one sensor. For this reason, in the determination method of the embodiment, for example, the leg having the problem may be determined based on the measured result of the acceleration and the measured result of the angular velocity sensor that are one 6-axis sensor or one 9-axis sensor and attached to the chest.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A method for managing health condition, comprising:
   detecting, by a computer, a grounding timing of a leg of a quadruped by using a first sensor;
   detecting, by the computer, a timing of weight-shift to a rear side of the quadruped by using a second sensor which is mounted at a bottom position of a breast collar hung around a neck of the quadruped; and
   determining whether or not the leg of the quadruped has a disease or injury, based on the detected grounding timing of the leg of the quadruped and the detected timing of a weight-shift to the rear side of the quadruped.

2. The method for managing health condition according to claim 1, wherein the process includes detecting a peak acceleration in a vertically upward direction in a vertical direction component of an acceleration data, as the timing of the weight-shift to the rear side of the quadruped based on the acceleration data measured by an acceleration sensor corresponding to the second sensor.

3. The method for managing health condition according to claim 1, wherein the process includes detecting a peak acceleration in a vertically downward direction in a vertical direction component of an acceleration data as the timing of the grounding timing of the leg of the quadruped based on the acceleration data measured by an acceleration sensor mounted on the abdomen or chest of the quadruped and corresponding to the first sensor.

4. The method for managing health condition according to claim 3, wherein the quadruped is a horse, and further comprising: the process includes determining which leg of the right and left front legs of the quadruped is the leg being grounded based on information relating to a positional relationship in a front-back direction of a horse body between a right side leg and a left side leg of the horse, and an acceleration change in the vertical direction between peaks of acceleration in the vertically downward direction of the quadruped.

5. The method for managing health condition according to claim 1, wherein specifying a leg in which the grounding timing is detected immediately before the timing of the weight-shift to the rear side as a leg having a disease or injury.

6. The method for managing health condition according to claim 1, wherein the first sensor includes a right sensor mounted a right side of an abdomen of the quadruped and a left sensor mounted a left side of the abdomen of the quadruped.

7. A health condition management apparatus comprising:
   a first sensor mounted on a quadruped and configured to detect a grounding timing of a leg of a quadruped;
   a second sensor mounted at a bottom position of a breast collar hung around a neck of the quadruped and configured to detect a timing of weight-shift to a rear side of the quadruped;
   a processor configured to determine whether or not the leg of the quadruped has a disease or injury based on a detected grounding timing of the leg of the quadruped and a detected timing of weight-shift to the rear side of the quadruped.

8. The health condition management apparatus according to claim 7, wherein the processor determines whether or not the leg of the quadruped has a disease or injury by using a timing of a peak that exceeds a preset threshold among peaks of acceleration in a vertically upward direction in a vertical direction component of acceleration data measured by an acceleration sensor corresponding to the second sensor, as the timing of the weight-shift to the rear side of the quadruped.

9. The health condition management apparatus according to claim 7, wherein the processor determines whether or not the leg of the quadruped has a disease or injury by using a peak of acceleration in a vertically downward direction in the vertical direction component of acceleration data measured by an acceleration sensor mounted on the abdomen or chest of the quadruped, as the grounding timing of the leg of the quadruped and corresponding to the first sensor.

10. The health condition management apparatus according to claim 7, wherein the processor specifies the leg of the quadruped in which the grounding timing is detected immediately before the timing of the weight-shift to the rear side of the quadruped, as a leg having a disease or injury.

11. The health condition management apparatus according to claim 7, wherein the first sensor includes a right sensor mounted a right side of an abdomen of the quadruped and a left sensor mounted a left side of the abdomen of the quadruped.

12. A health condition management system comprising:
   a health condition management apparatus that manages a health condition of a leg of a quadruped;
   a first sensor that detects a grounding of the leg of the quadruped; and
   a second sensor that is mounted at a bottom position of a breast collar hung around a neck of the quadruped and detects weight-shift to a rear side of the quadruped,
   wherein the health condition management apparatus includes a processor that determines whether or not the leg of the quadruped has a disease or injury, based on the grounding timing of the leg of the quadruped detected by the first sensor and the timing of the weight-shift to the rear side of the quadruped detected by the second sensor.

13. The health condition management system according to claim 12, wherein the processor specifies the leg having a disease or injury when determining whether or not the leg of the quadruped has a disease or injury.

14. The health condition management system according to claim 13, wherein the processor specifies the leg of the quadruped of which the grounding timing is detected immediately before the timing of the weight-shift to the rear side of the quadruped, as a leg having a disease or injury.

15. The health condition management system according to claim 12, wherein the first sensor includes a right sensor mounted a right side of an abdomen of the quadruped and a left sensor mounted a left side of the abdomen of the quadruped.

* * * * *